United States Patent
Serie et al.

(10) Patent No.: US 11,869,634 B2
(45) Date of Patent: Jan. 9, 2024

(54) AUTOMATED DETECTION OF BOUNDARIES IN MASS SPECTROMETRY DATA

(71) Applicant: VENN BIOSCIENCES CORPORATION, South San Francisco, CA (US)

(72) Inventors: Daniel Serie, San Mateo, CA (US); Zhenqin Wu, Palo Alto, CA (US)

(73) Assignee: VENN BIOSCIENCES CORPORATION, South San Francisco, CA (US)

( * ) Notice: Subject to any disclaimer, the term of this patent is extended or adjusted under 35 U.S.C. 154(b) by 958 days.

(21) Appl. No.: 16/833,324

(22) Filed: Mar. 27, 2020

(65) Prior Publication Data

US 2020/0372973 A1 Nov. 26, 2020

Related U.S. Application Data

(60) Provisional application No. 62/826,228, filed on Mar. 29, 2019.

(51) Int. Cl.
*G16B 40/00* (2019.01)
*G16B 5/00* (2019.01)

(52) U.S. Cl.
CPC .............. *G16B 40/00* (2019.02); *G16B 5/00* (2019.02)

(58) Field of Classification Search
CPC .................................. G16B 40/00; G16B 5/00
USPC ........................................ 250/281, 282, 283
See application file for complete search history.

(56) References Cited

U.S. PATENT DOCUMENTS

| 2018/0179499 A1* | 6/2018 | Lau ................ C12Y 203/03014 |
| 2019/0101544 A1 | 4/2019 | Danan-Leon et al. |
| 2020/0132697 A1* | 4/2020 | Yan .................... G01N 33/6848 |

FOREIGN PATENT DOCUMENTS

| WO | WO 2019/046814 A1 | 3/2019 |
| WO | WO 2019/079639 A1 | 4/2019 |
| WO | WO 2020/160515 A1 | 8/2020 |
| WO | WO 2020/205649 A1 | 8/2020 |

OTHER PUBLICATIONS

International Preliminary Report on Patentability, dated Sep. 28, 2021, mailed Jul. 20, 2020, for PCT Application No. PCT/US2020/025502, filed Mar. 27, 2020, 16 pages.
International Search Report and The Written Opinion of The International Searching Authority dated Jul. 20, 2020, for International Patent Application No. PCT/US2020/025502, filed Mar. 27, 2020, 20 pages.

(Continued)

*Primary Examiner* — Nicole M Ippolito
(74) *Attorney, Agent, or Firm* — Morrison & Foerster LLP

(57) ABSTRACT

A system and method for automated detection of the presence or absence of a quantity based on intensities expressed in terms of, or derived from frequency or time dependent data. According to one example intensities from mass spectrometry are identified using a non-linear mathematical model, such as an artificial neural network trained to find start and stop peaks of an intensity, from which an abundance may be determined.

21 Claims, 25 Drawing Sheets

(56) References Cited

OTHER PUBLICATIONS

Skarysz, A et al. (2018). "Convolutional Neural Networks For Automated Targeted Analysis of Raw Gas Chromatography-Mass Spectrometry Data," 2018 International Joint Conference on Neural Networks (IJCNN), Rio de Janeiro, Brazil, 9 pages.
Aoshima et al., "A simple peak detection and label free quantitation algorithm for chromatography-mass spectrometry", BMC bioinformatics, 2014, 15(1):376, 14 pages.
Bereman et al., "The development of selected reaction monitoring methods for targeted proteomics via empirical refinement", Proteomics, 2012, 12(8), pp. 1134-1141; DOI 10.1002/pmic.201200042.
Demichev et al., "DIA-NN: Neural networks and interference correction enable deep coverage in high-throughput proteomics", bioRxiv, Oct. 25, 2018, XP055696494, DOI: 10.1101/282699.
Eshghi et al., "Quality assessment and interference detection in targeted mass spectrometry data using machine learning", Clinical Proteomics, vol. 15, No. 33, 2018, pp. 1-13.
Gallant et al., "Deconvolution of overlapping chromatographic peaks using a cerebellar model arithmetic computer neural network", Chemometrics and Intelligent Laboratory Systems, Elsevier Science Publishers B.V., Amsterdam, NL, vol. 18, No. 1, Jan. 1, 1993, pp. 41-57.
Kessner et al., "ProteoWizard: open source software for rapid proteomics tools development", Bioinformatics, 2008, 24(21), pp. 2534-2536; doi:10.1093/bioinformatics/btn323.
Li et al., "Site-Specific Glycosylation Quantitation of 50 Serum Glycoproteins Enhanced by Predictive Glycopeptidomics for Improved Disease Biomarker Discovery", Analytical Chemistry, 2019, 91, pp. 5433-5445.
Maclean et al., "Skyline: an open source document editor for creating and analyzing targeted proteomics experiments", Bioinformatics, 2010, 26(7), pp. 966-968.
Rost et al., "Openms: a flexible open-source software platform for mass spectrometry data analysis", Nature Methods, Sep. 2016, vol. 13, No. 9, pp. 741-748.
Tran et al., "Deep learning enables de novo peptide sequencing from data-independent-acquisition mass spectrometry", Nature Methods, vol. 16, No. 1, Jan. 2019, pp. 63-66.
Tsou et al., "Dia-Umpire: comprehensive computational framework for data-independent acquisition proteomics", Nature Methods, Mar. 2015, 2(3), pp. 258-264; doi:10.1038/nmeth.3255.
Zohora et al., "DeepIso: A Deep Learning Model for Peptide Feature Detection", arxiv.org, Cornell University Library, 201, Olin Library Cornell University Ithaca, NY, 14853, Dec. 9, 2017; XP081203333.
Supplementary Note 1: Overview Of OpenM; Supplementary Note 2: Available Tools; Supplementary Note 3: Case Studies; The OpenMS Developers; Nature Methods: doi:10.1038/nmeth.3959; 147 pages.

\* cited by examiner

AUTOMATED DETECTION OF BOUNDARIES IN MASS SPECTROMETRY DATA

CROSS-REFERENCE TO RELATED APPLICATIONS

This application claims priority to, and the benefit of, U.S. Provisional Patent Application No. 62/826,228, filed Mar. 29, 2019, the entire contents of which are herein incorporated by reference in its entirety for all purposes.

FIELD

This disclosure is generally related to detection of physical things using mass spectrometry and, in particular, the automated detection of a biological quantity using multiple reaction monitoring mass spectrometry (MRM-MS).

BACKGROUND

Multiple reaction monitoring (MRM) is a technique utilized in tandem mass spectrometry (MS) which allows for highly sensitive and specific detection of proteins, lipids, and post-translational modifications (PTMs), among other analytes. This technology holds great promise for use in new clinical assays and diagnostics, but the availability of precise analytical software remains a bottleneck.

Traditional analysis of MRM experiments involved choosing the start and stop of a chromatographic peak by hand, working from transitions previously characterized by data-dependent acquisition or other discovery techniques. A typical implementation can be seen in Agilent's MassHunter software, where intensities are plotted over a pre-specified range of retention times (RT) for a given precursor and product mass-to-charge ratio. Selection of the beginning and end of the peak yields an observed RT, peak width, and integrated abundance value. Person to person variability in assessment, human error, and a large time investment render this method inadequate for non-research use. In recent years many software packages have attempted to fill this gap by automatically integrating peaks from a list of transitions.

The existing software packages have proven very useful in quantifying, e.g., peptides, when there is a high relative abundance present in the mass spectrometry data. But these software packages are less accurate in integrating relatively low-abundant and highly-heterogeneous species such as glycosylated peptides.

SUMMARY

The instant disclosure sets forth methods and systems for automated detection of the presence of a quantity expressed in terms of, or derived from time series data. The instant disclosure also sets forth methods and systems for automated detection of the presence of a quantity expressed in terms of, or derived from frequency-dependent data.

In one implementation, automated detection is applied to a time series of intensities vs. time. The intensities derive from a detector which detects the presence or absence of a quantity. For example, the automated detection may be applied to mass spectrometry (MS) in which the intensities derive from a MS detector detecting a transition value as a function of time, e.g., retention time. As such, the automated detection described herein may be applied to a wide variety of data inputs based on intensity values observed as a function of time or as a function of frequency.

In one implementation the automated detection is applied to a time series of mass to charge ratio intensities vs. time, which were produced from a process involving mass spectrometry (MS). In another implementation the automated detection is applied to a time series of intensities vs. time, which were produced from a process involving liquid or gas chromatography.

According to other examples the automated detection may be applied to any of the following intensities expressed in terms of, or derived from time or frequency data:

x-ray diffraction in which the intensities derive from an x-ray detector, e.g., charge coupled device (CCD), detecting a reflection of x-rays as a function of the x-ray scan angle, e.g., 2-$\Theta$, in which scan angles are observed as a function of time.

Raman spectroscopy in which the intensities derive from an infrared detector detecting vibrational modes as a function of light wavelength, e.g., $cm^{-1}$, absorption or emission.

UV-VIS spectroscopy in which the intensities derive from a light detector detecting intensities of electronic transitions as a function of ultra-violet and visible light wavelengths or frequencies. fluorimetry spectroscopy or phosphorimetry spectroscopy in which emitted fluorescence and phosphorescence light intensity is detected as a function of incident, i.e., absorbed or excitation, wavelength.

Nuclear Magnetic Resonance (NMR) spectroscopy in which the intensities derive from a radio wave detector detecting nuclear transitions as a function of radiation frequency absorption or emission within a strong magnetic field. In NMR, the intensity v. frequency detection can be converted, e.g., using Fourier transformations, into an equivalent intensity v. time. The same principles applicable to NMR are also applicable to Magnetic Resonance Imaging (MRI).

In one particular implementation automated detection is applied to a time series of mass to charge ratio intensities vs. time, which were produced from a process involving mass spectrometry. According to this implementation the automated detection involves using one or more mathematical models to detect where a start peak and end peak occurs in MS data. By providing an accurate selection of these boundary points a more accurate assessment of an abundance is made.

According to one aspect, a method of training a machine learning model to identify mass spectrometry peaks uses as a training set sequences of points representing mass/charge ratios where the peak starts and peak stops are labeled. The trained model is adapted for identifying mass spectrometry start and stop peaks indicating the presence of one or more glycopeptides or peptides, or a fragment thereof, present in a biologic sample.

According to another aspect, a method of identifying mass spectrometry peaks uses at least one trained neural network model that produces an output as a function of input parameters, wherein values for the input parameters may be a sequence of retention time values for a glycopeptide having a m/z (mass to charge) ratio.

According to another aspect, raw MS data is featurized to produce training sets for a machine learning model for purposes of training the model to identify peak start and stop times in MS data. The featurization may include discretizing an analog sample of MS data into a sequence of points, wherein retention times corresponding to peak areas in the analog sample are left out of the sequence of points, and assigning labels to points among the sequence of points corresponding to peak start and peak stop times to produce a labeled sequence of points. The labels may be found using human annotators trained to select peak start and stop times using a display and input device.

According to another aspect, a method computes a distribution of probabilities over a sequence of points representing MS data for a given m/z ratio and retention time period, the probabilities representing a likely peak start or peak stop retention time. From these distribution of probabilities a statistic for an abundance is computed. The statistic may be a mean.

According to another aspect, a method of diagnosing a disease includes quantifying mass spectrometry transitions, wherein the transitions are m/z intensity value peaks characteristic of glycopeptides or peptides, or a fragment thereof, comprising an amino acid sequence and analyzing the quantification using a model to determine a probability that the sample is or isn't within a disease classification based on the quantification. In some examples, the glycopeptides or peptides, or a fragment thereof, comprising an amino acid sequence are selected from those sequences set forth in International Patent Application Publication No. WO 2019/046814—Identification and use of glycopeptides as biomarkers for diagnosis and treatment monitoring; International Patent Application Publication No. WO2019079639A1—Identification and use of biological parameters for diagnosis and treatment monitoring; US Patent Application Publication No. US20190101544A1—Identification and use of glycopeptides as biomarkers for diagnosis and treatment monitoring; International PCT Patent Application No. PCT/US2020/0162861, filed Jan. 31, 2020; and also U.S. Provisional Patent Application No. 62/989,510, filed Mar. 13, 2020. The entire contents of each of these patent applications is herein incorporated by reference in its entirety for all purposes.

BRIEF DESCRIPTION OF THE DRAWINGS

In FIG. 6C, the sample peak and reference-based model predictions are for the MRM transition for SEQ ID NO:1 in International PCT Patent Application No. PCT/US2020/0162861, filed Jan. 31, 2020, which is herein incorporated by reference in its entirety for all purposes, and its reference peak illustrated in lower right panel, and attention map (extracted from the model) in lower left panel.

FIGS. 11A and 11B are scatter plots comparing abundance calculations between MODEL A and MODEL B, respectively. Scatter plot of peak abundance prediction/annotation from sequential (A) and reference-based (B) neural network. In sequential model predictions, weighted abundances (purple points) show higher consistency with ground truth and less outliers than argmax abundances (blue points), with a higher Pearson's r at 0.9969. Note that weighted abundances are biased upwards in low-abundance range. While in reference-based predictions results are highly similar.

FIG. 13 shows for MODEL A histogram of prediction confidences, mean absolute errors of boundary predictions and scatter plots for different confidence score bins.

FIG. 14 shows for MODEL B histogram of prediction confidences and mean absolute errors of boundary predictions.

DETAILED DESCRIPTION

Figure 1:
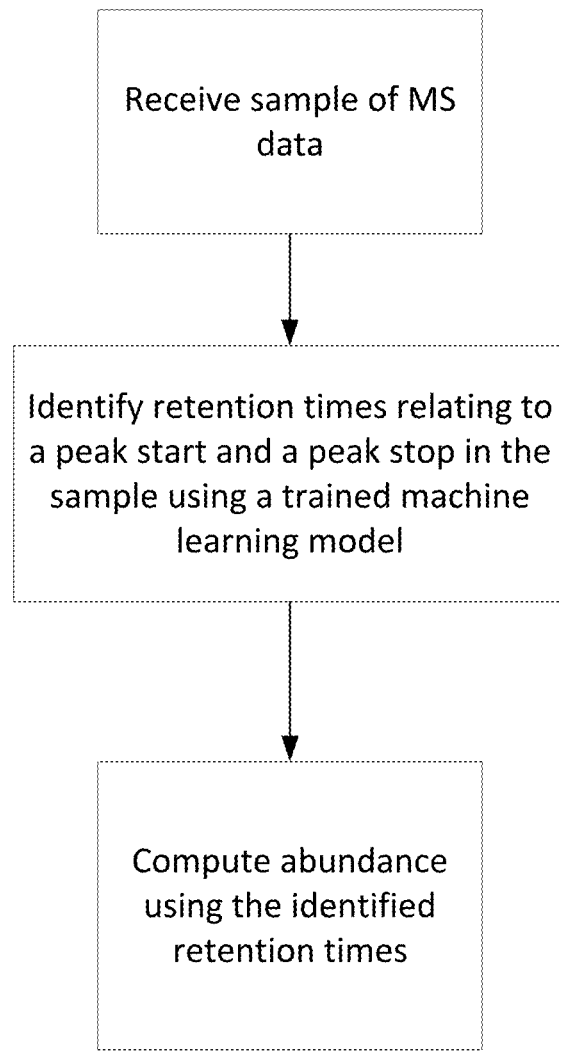
FIG. 1 shows a process for calculating an abundance from mass-spectrometry data using a machine learning model.

In the description like reference numbers appearing in the drawings and description designate corresponding or like elements among the different views.

Definitions

As used in the present specification, the following words and phrases are intended to have the meanings as set forth below, except to the extent that the context in which they are used unambiguously indicates otherwise.

A "transition" refers to a temporal sequence of mass-to-charge ratio intensities from mass spectrometry. As used herein, the phrase a "transition" or a "multiple-reaction-monitoring (MRM) transition," refers to the mass to charge (m/z) peaks or signals observed when a glycopeptide, or a fragment thereof, is detected by MRM-MS. The MRM transition is detected as the transition of a precursor and product ion. The time interval for transition detection is dependent on the feed rate of the tandem liquid chromatography instrument and the flow rate within the MRM spectrometer.

A "biologic quantity" is understood as meaning an amount of an analyte in a biological sample or amount of a solute in a tandem chromatography instrument. Analytes and solutes include, but are not limited to, glycans, peptides, glycopeptides, glycosylated peptides, proteins, glycoproteins, and fragments thereof.

As used herein, the phrase "biological sample," refers to a sample derived from, obtained by, generated from, provided from, take from, or removed from an organism; or from fluid or tissue from the organism. Biological samples include, but are not limited to synovial fluid, whole blood, blood serum, blood plasma, urine, sputum, tissue, saliva, tears, spinal fluid, tissue section(s) obtained by biopsy; cell(s) that are placed in or adapted to tissue culture; sweat, mucous, fecal material, gastric fluid, abdominal fluid, amniotic fluid, cyst fluid, peritoneal fluid, pancreatic juice, breast milk, lung lavage, marrow, gastric acid, bile, semen, pus, aqueous humor, transudate, and the like including derivatives, portions and combinations of the foregoing. In some examples, biological samples include, but are not limited, to blood and/or plasma. In some examples, biological samples include, but are not limited, to urine or stool. Biological samples include, but are not limited, to saliva. Biological samples include, but are not limited, to tissue dissections and tissue biopsies. Biological samples include, but are not limited, any derivative or fraction of the aforementioned biological samples.

As used herein, the term "glycan" refers to the carbohydrate residue of a glycoconjugate, such as the carbohydrate portion of a glycopeptide, glycoprotein, glycolipid or proteoglycan.

As used herein, the term "glycopeptide," refers to a peptide having at least one glycan residue bonded thereto.

As used herein, the phrase "glycosylated peptides," refers to a peptide bonded to a glycan residue.

As used herein, the phrase "glycopeptide fragment" or "glycosylated peptide fragment" refers to a glycosylated peptide (or glycopeptide) having an amino acid sequence that is the same as part (but not all) of the amino acid sequence of the glycosylated protein from which the glycosylated peptide is obtained by digestion, e.g., with one or more protease(s) or by fragmentation, e.g., ion fragmentation within a MRM-MS instrument. MRM refers to multiple-reaction-monitoring.

As used herein, the phrase "fragmenting a glycopeptide," refers to the ion fragmentation process which occurs in a MRM-MS instrument. Fragmenting may produce various fragments having the same mass but varying with respect to their charge.

As used herein, the phrase "multiple reaction monitoring mass spectrometry (MRM-MS)," refers to a highly sensitive and selective method for the targeted quantification of glycans and peptides in biological samples. Unlike traditional mass spectrometry, MRM-MS is highly selective (targeted), allowing researchers to fine tune an instrument to specifically look for certain peptides fragments of interest. MRM allows for greater sensitivity, specificity, speed and quantitation of peptides fragments of interest, such as a potential biomarker. MRM-MS involves using one or more of a triple quadrupole (QQQ) mass spectrometer and a quadrupole time-of-flight (qTOF) mass spectrometer.

As used herein, "peptide," is meant to include glycopeptides unless stated otherwise.

"Retention time (RT)" is understood as meaning the time taken for a solute to pass through a chromatography column. It is calculated as the time from injection to detection. RT depends on several factors, including but not limited to, the gas flow rate; temperature differences in the oven and column; column degradation; column length; column type and carrier gas.

Mass Spectrometry (MS) data or datasets is understood as meaning a collection of spectra plotting intensity of transitions as a function of transition number. MS data for a given transition value is mass (m) over charge (z) intensity levels (m/z) over a time period (t), which is the retention time (RT).

An "abundance" is understood as meaning a computed amount of some biologic quantity represented in mass spectrometry data. An abundance may be computed by summing values at discrete time points between a start and stop peak boundary. Abundance may also be computed by integration over discrete time steps between the start and stop peak boundary. Integration may be performed by any standard method, e.g., $\Sigma(t_{i+1}-t_i)*(\frac{1}{2})*[I(t_i)+I(t_{i+1})]$, $i=1 \ldots n-1$ (n is the number of discrete points between boundaries, $I(t_i)$ is mass-to-charge intensity at retention time $t_i$). Unless specified otherwise, abundance refers to relative abundance of one integrated MRM peak relative to another MRM peak.

The mathematical models that may be developed to practice aspects of the invention are limited to non-linear mathematical models in the sense that the non-linearity results in there being no set of optimized function/model parameters based on finding a global minimum value; rather, an optimized function/model parameters resides only in a local minimum (no global minimum exists). The model architectures contemplated include, but are not limited to, artificial neural networks, graph models and support vector machines.

A "machine learning model" or "learning model" is understood as meaning any variety of mathematical model having at least one non-linear activation layer (in addition to one or more affine transformations). A machine learning model is moreover trained or optimized via minimization of one or more loss functions (e.g., minimization of cross-entropy loss or negative log-likelihood) that are separate from the model itself. A training or optimization process seeks to optimize the model to reproduce a known outcome (low bias) as well as enabling the model to make accurate predictions from unseen experiences (low variance). The model's output may be any variety of things relevant to the task, e.g., a probability or statistic, classification, sequence, etc. In one particular example, data used to train and optimize the model is sequential data such as time-series data where a target outcome is known, which sequential data with known target outputs is taken to mean labeled or annotated sequential data.

An example of a well-known model suited to make predictions based on labeled sequential data is a one-directional, or bi-directional recurrent neural network (RNN) with long short term memory (LSTM) units or gated recurrent units (GRUs), and optionally with an attention mechanism. An attention mechanism (or attention layer) may retain more important information from past state variables to influence a future state prediction than what may be possible in a final LSTM unit or GRU of a sequence, or a combination of LSTM units or GRUs along with a bi-directional RNN that represents the accumulated knowledge from past states. A attention mechanism applies learned weights to each of the input states to emphasize less or more important features of the input MS data points appearing in the sequence when generating output predictions. These learned weights are more or less directly coupled to each of the corresponding output states, or the final output state depending on the desired output.

Models that are trained and optimized using only labeled data are known as supervised models. Learning models may also be unsupervised or semi-supervised models. These models are trained and optimized using un-labeled data or a combination of labeled and unlabeled data. Models that are trained and optimized using combinations of labeled and unlabeled data or primarily un-labeled data are known as semi-supervised and unsupervised models, respectively. A learning model may be efficiently trained and optimized by the well-known approach of stochastic gradient descent (SGD). The learning model's hyper-parameters may be optimized by manual adjustment during training and/or validation, or learned by way of minimizing a surrogate loss function with respect to one or more of the hyperparameters, in parallel with the minimization of the learning model's global loss function.

A "training set" is a dataset used to train or tune parameters in a learning model to reproduce a known, targeted output.

A "validation set" is a dataset used to tune the model's predictive capabilities against new experiences to arrive at an optimal balance between matching the labeled data (low bias) and predicting start/stop locations for unseen transitions (low variance). The validation set is applied after the model has been tuned based on the training set.

A "test set" (or leave-out validation set) is a dataset used to evaluate the optimized model's predictive capabilities. The model's performance against the test set is the metric used to assess the model's ability to make an accurate prediction for new, unseen transitions.

"Featurization" is understood as meaning processes associated with converting raw data representing samples from a distribution for use as input to a machine learning model. Examples of featurization include discretization of an analog signal into a digital signal, filtering or de-noising or clipping parts of data (e.g., reducing signal-to-noise ratio), normalizing signals and standardization of signals (e.g., centering a target peak within a window). Featurization may also include introducing noise into a data set for purposes of validating a model or related augmentation of samples for generalization and/or improving a model's ability to make predictions from new (or unseen) experiences.

According to the disclosure the dataset of sequential data from which training, validation and test datasets were sampled may include at least labeled start and stop locations for transitions, each of which locations indicate boundary points for computing an abundance by integration between the boundary points. In a preferred embodiment the targeted output are probabilities of start and stop locations for each point in the sequential data of a transition.

Discussion

As mentioned earlier, traditional analysis of MRM experiments involves choosing a start and stop of a chromatographic peak by hand and working from transitions previously characterized by data-dependent acquisition or other discovery techniques. Software suites, such as Agilent's MassHunter software, plot signal intensities over a pre-specified range of retention times (RT) for a given precursor and product mass-to-charge ratio. Manual selection of the beginning and end of the peak yields an observed RT, peak width, and integrated abundance value. Person to person variability in assessment, human error, and a large time investment however render this method inadequate for non-research use.

For transitions characterized by clearly defined single peaks and high signal-to-noise ratio, the above manual process of picking boundary points for computing abundances may be effective, but this method may not provide accurate or produce consistent results when detecting abundances for biologic quantities characterized by a low signal-to-noise ratio.

Referring to FIG. 1, according to the disclosure a trained machine learning model is instead used to automatically select boundary points in mass spectra for a specified retention time window and mass/charge intensity. The input to the machine learning model is a sequence of points (sample of MS data). Each point represents a mass/charge intensity for a corresponding retention time.

Figure 2:
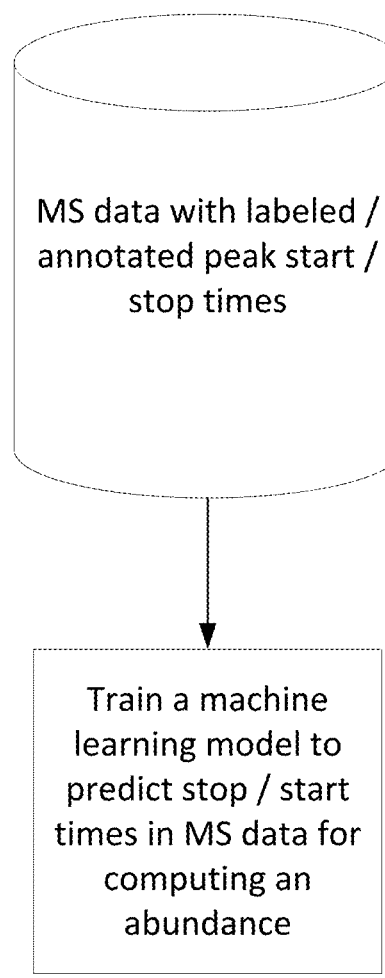
FIG. 2 shows a process for training the machine learning model of FIG. 1. Model performances on test set. A: Bar plot of absolute error in boundary predictions on test set. B: Cumulative distributions of boundary prediction errors. Note that 19039 (28.1%) samples are out of range (>6 seconds) in rule-based predictions, 4824 (7.1%) samples in Sequential NN, 1470 (2.2%) samples in Reference-based NN. C: Scatter plot of peak abundance prediction/annotation on the test set.

Referring to FIG. 2, according to one implementation the machine learning model is a neural network that produces probabilities of peak start and peak stop times for each of the corresponding points provided as input. The neural network is trained using mass spectra that has target peak start and stop retention times labeled. Through a training and validation process the optimal model parameters are found. The labeled data may be obtained from human annotators selecting peak start/stop times using a graphical user interface and input device.

Figure 3:
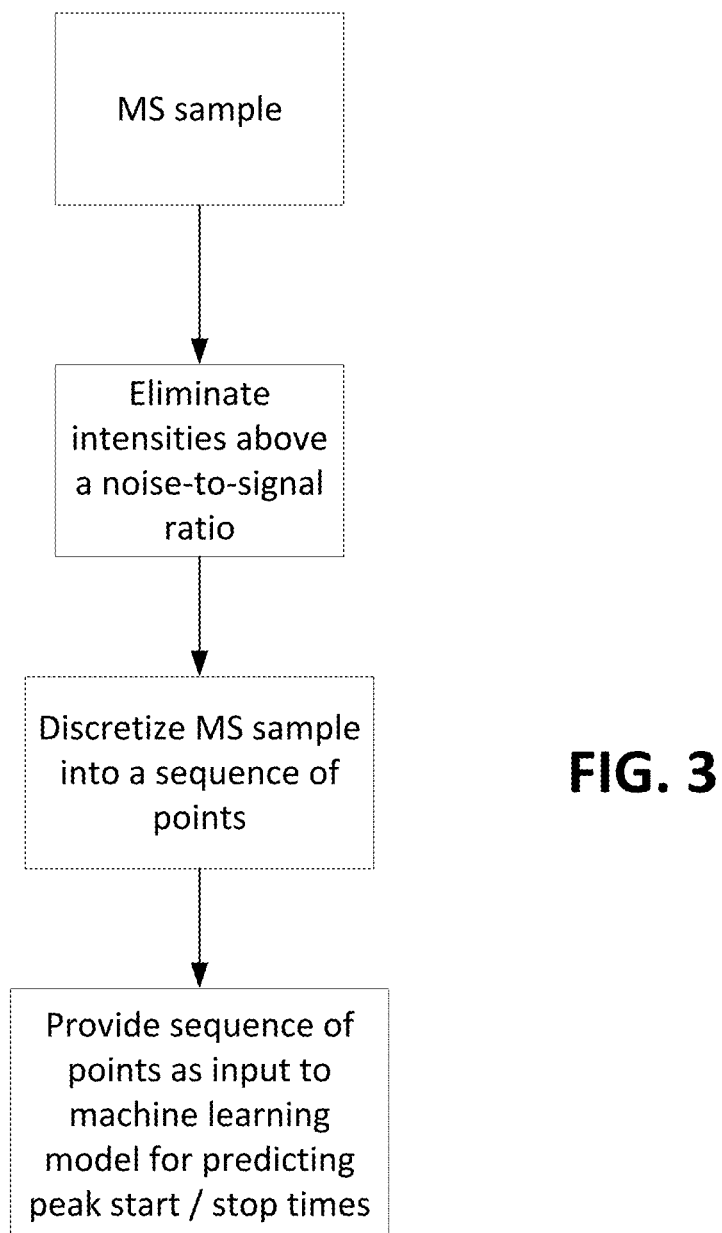
FIG. 3 shows a process for generating a sequence of points from MS sample used as input to the machine learning model of FIG. 2.

Referring to FIG. 3 there is a process flow for featurizing raw mass spectra data for input to the machine learning model of FIG. 1. The featurization steps may include (1) remove mass/charge intensities above a certain threshold amount or, alternatively, choosing only those points that are mostly noise and near a signal-to-noise transition region of the MS data; and (2) discretizing the analog signal into a set of points to produce sequential data.

Figure 4:
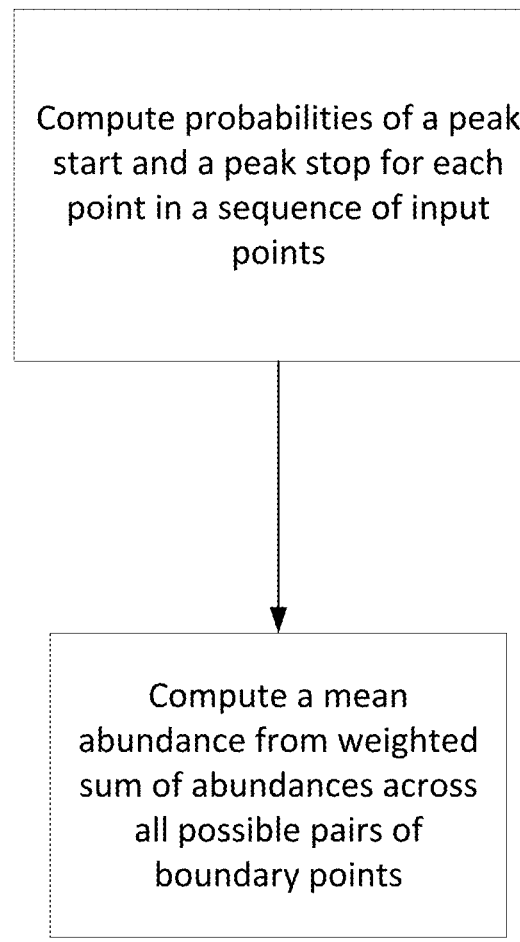
FIG. 4 is a process for computing an abundance based on computed probabilities of peak start and peak stop retention times in an MS sample.

Referring to FIG. 4, in one particular implementation the model computes an abundance amount based on a weighted sum of integrals. One of the most direct ways is to interpret the machine learning model's prediction outcomes as probability distributions. In other words, to have the model evaluate probabilities of all possible pairs of points in a sequence that could serve as peak start/end markers. For a sequence of N points, this involves in total $N \times (N-1)/2$ pairs after imposing the order constraint. Each pair's probability can be easily calculated by multiplying prediction values of the peak start/end tasks on the two points. The probabilities are then used to calculate a weighted sum over the integrals between corresponding pairs, providing a mean estimate instead of a single abundance value calculated from the two end points having the highest probability of being the true boundary. A mean of the abundances may provide more robust abundance estimates.

Embodiments

In some examples, set forth herein is a method of training a model to identify mass spectrometry peaks, comprising: using a plurality of labeled sequential data, each of the plurality of labeled sequential data comprising a peak start and a peak stop label representing retention time values characteristic of glycopeptides or peptides, or fragments thereof, and training at least one machine learning model using the labeled sequential data, wherein the trained model is adapted for identifying mass spectrometry start and stop peaks indicating the presence of one or more glycopeptides or peptides, or a fragment thereof, present in a biologic sample.

In some examples, including any of the foregoing, the method further comprises quantifying the presence of the one or more glycopeptides or peptides by integration over time between the mass spectrometry start and stop peaks from the biologic sample.

In some examples, including any of the foregoing, the machine learning model is a recurrent neural network model.

In some examples, including any of the foregoing, the recurrent neural network is a bi-directional LSTM recurrent neural network model with attention layer.

In some examples, set forth herein is a method comprising computing an abundance for a glycopeptide or peptide using a machine learning model trained a process set forth herein.

In some examples, set forth herein is a system, comprising a data repository of labeled sequential data; one or more processors coupled to the repository; machine executable code, residing in non-transitory memory accessible to the one or more processors, that when executed by the one or more processors performs a method set forth herein.

In some examples, set forth herein is a method of identifying mass spectrometry peaks, comprising: providing at least one trained neural network model that produces an output as a function of input parameters, wherein values for the input parameters comprise a sequence of retention time values for a glycopeptide having a m/z (mass to charge) ratio; and providing as values for the input parameters mass spectrometry (MS) data comprising mass-to-charge (m/z) ratios over the sequence of retention time values from a mass spectrometry of a biologic sample; wherein the output comprises a location for one or more peak start and peak stop retention time values indicating the presence of one or more analytes, or a fragment thereof, in the biologic sample.

In some examples, including any of the foregoing, the method further comprises quantifying the presence of the one or more glycopeptides or peptides by summing or integration over retention time values between the mass spectrometry start and stop peaks from the biologic sample.

In some examples, including any of the foregoing, the method further comprises quantifying the presence of the one or more glycopeptides or peptides by summing over retention time values between the mass spectrometry start and stop peaks from the biologic sample. In some examples, including any of the foregoing, the method further comprises quantifying the presence of the one or more glycopeptides or peptides by integration over retention time values between the mass spectrometry start and stop peaks from the biologic sample.

In some examples, including any of the foregoing, the quantifying step includes applying a weighted smoothing function over the predicted start and stop peaks.

In some examples, set forth herein is a system, comprising a data repository of mass spectrometry (MS) data; one or more processors coupled to the repository; machine executable code, residing in non-transitory memory accessible to the one or more processors, that when executed by the one or more processors performs a method set forth herein.

In some examples, set forth herein is a method comprising: featurizing data from raw MS data, wherein the raw MS data comprises a plurality of analog samples, each representing mass/charge intensity, the featurizing comprising, for each of the analog samples, the steps of centering the sample within a retention time window, discretizing the sample into a sequence of points representing intensity values, standardizing the intensity values, and assigning labels to points among the sequence of points corresponding to peak start and peak stop times to produce a labeled sequence of points; wherein the labeled sequence of points are configured for training a machine learning model to predict an abundance in unseen MS data.

In some examples, including any of the foregoing, the centering comprises positioning an apex of a curve at a center of the retention window.

In some examples, including any of the foregoing, the standardizing the intensity values excludes intensity values greater than a threshold amount. In some examples, including any of the foregoing, the threshold amount is about 500.

In some examples, set forth herein is a system, comprising a data repository of raw mass spectrometry (MS) data comprising a plurality of analog samples; one or more processors coupled to the repository; machine executable code, residing in non-transitory memory accessible to the one or more processors, that when executed by the one or more processors performs the method of any In some examples, set forth herein is a method, comprising computing a distribution of probabilities over a sequence of points representing mass spectrometry (MS) data for a given m/z ratio and retention time period, the probabilities representing a likely peak start or peak stop retention time, and computing a statistic for the abundance using the distribution of probabilities, wherein the statistic is indicative of the presence of a biologic sample in the MS data.

In some examples, including any of the foregoing, the statistic is a mean abundance computed as a weighted sum of integrals using all possible pairs of start and end points for evaluating the integral.

In some examples, including any of the foregoing, the machine learning model is a sequential model (MODEL A) or a reference-based model (MODEL B).

In some examples, set forth herein is a method, comprising: using a plurality of labeled sequential data, and training at least one machine learning model using the labeled sequential data, wherein the trained model is adapted for identifying a time period or frequency range where a start and stop peak of an intensity occur in an unseen sample.

In some examples, including any of the foregoing, the start and stop peak is contained in a noise to signal transition time period.

In some examples, including any of the foregoing, the machine learning model is a recurrent neural network with an attention layer.

In some examples, including any of the foregoing, the sample represents a physical thing such that a summation or integration over time or frequency from the start peak to the stop peak of the intensity quantifies the physical thing.

In some examples, including any of the foregoing, the sample is a sequential series of mass to charge intensities over a specified time period and the summation or integration represents the abundance of the physical thing.

In some examples, set forth herein is a method, comprising: providing at least one trained neural network model that produces an output as a function of input parameters, wherein values for the input parameters are a temporal or spectral sequence of intensity values representing a quantity; and providing values for each of the input parameters, the values representing an unseen sequence of intensities for a quantity; wherein the output comprises one or more peak start and peak stop times or frequencies, which are used to quantify the quantity.

In some examples, including any of the foregoing, the quantity is quantified by summing or integration over time or frequency between the peak start and peak stop times or frequencies, respectively.

In some examples, including any of the foregoing, the intensities are obtained from a process selected from the set of mass spectrometry, MRM, liquid or gas chromatography, x-ray diffraction, Raman spectroscopy, UV-VIS spectroscopy, fluorimetry spectroscopy or phosphorimetry spectroscopy, Nuclear Magnetic Resonance (NMR) spectroscopy, or Magnetic Resonance Imaging (MRI).

EXAMPLES

The following example describes a study conducted in accordance with several aspects of the disclosure.

In this study two learning models were trained, validated, and then tested to assess accuracy in predicting the location of peaks (or more precisely, the start/stop boundaries of peaks in order to compute more accurately an abundance for the associated transition). The particular architecture chosen for the learning model was a bi-directional recurrent neural network with long short term memory units and attention layer (RNN-LSTM-AL). The model architecture and training method is illustrated in FIGS. 5A, 5B, 6A, 6B and 6C. The model's input parameters or input state variables correspond to a temporal sequence representing mass-to-charge ratio (m/z) intensities.

The study accessed a large dataset of manually-labeled peaks from Mass Spectrometry (MS) transitions spanning a wide dynamic range, including both peptides and intact glycopeptides. This dataset contained the temporal sequence of intensities within each transition's Retention Time (RT). Each one of these transitions is a sequential data input to the RNN-LSTM-AL, and the associated human-annotated (or labeled) start and stop RT (indicating boundary points for integration to derive abundance) included with each one of the training, validation, and test transitions are the labels used for supervised learning, validation and testing, respectively.

2.1 Data Sets

Two mass spectrometry datasets were used for the study. Raw Agilent QQQ MS output for the first experiment consisted of 716 transitions assessed in 210 human serum samples, which yielded 106355 valid sample peaks after filtering for positive abundance and RT shift. This set was split into a training set with 572 transitions and a validation set with 144 peaks.

The second experiment used MS output generated from 135 human serum samples purchased from a commercial biorepository. 503 transitions were evaluated, yielding 67672 high quality peaks that were used exclusively for testing. 313 test set transitions were not present in the train/validation set. The 313 test set transitions were used to compare model output predictions.

2.2 Baseline Method

The performance of the trained and validated RNN-LSTM-AL models were compared to two baseline predictors. The first of these baseline predictors is Skyline, which is a well-known open-source software tool used for data analysis of mass spectrometry applications including multiple reaction monitoring. The Skyline software calculates peak areas (abundances) of test samples. The second baseline predictor for comparison with the RNN models is a deterministic method of prediction and will hereinafter be referred to as the "rule-based" method. The architecture for the rule-based method is described in Ken Aoshima, Kentaro Takahashi, Masayuki Ikawa, Takayuki Kimura, Mitsuru Fukuda, Satoshi Tanaka, Howell E Parry, Yuichiro Fujita, Akiyasu C Yoshizawa, Shin-ichi Utsunomiya, et al. *A simple peak detection and labelfree quantitation algorithm for chromatography-mass spectrometry*. BMC bioinformatics, 15(1):376, 2014. The rule-based method model was developed for this study by tuning its model parameters to maximize train and validation set performances. And these tuned parameters were then applied during test set evaluations.

2.3 Sequential Models for Peak Integration

The RNN-LSTM-AL architecture was selected for making predictions from sequences of MS data in the study.

Figure 5A:
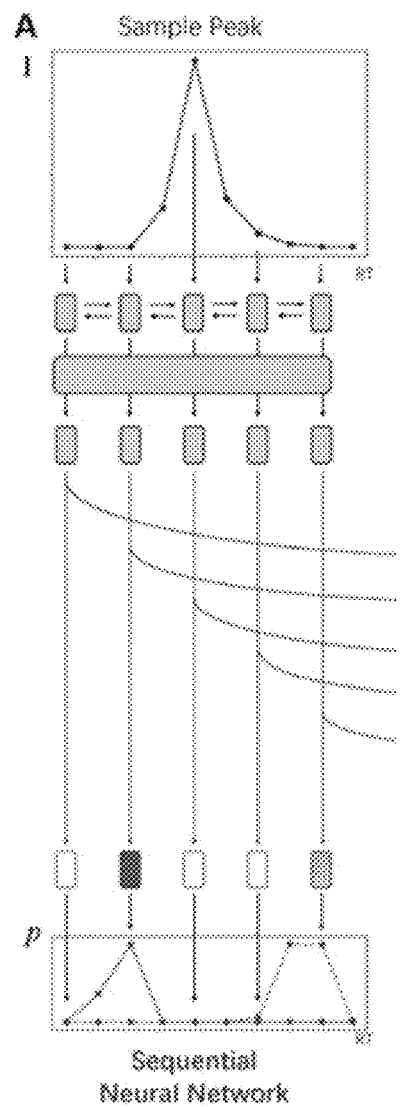
FIGS. 5A and 5B show a model architecture for a first machine learning model (MODEL A) that is a bi-directional recurrent neural network with long short term memory units and attention layer.
Figure 5B:
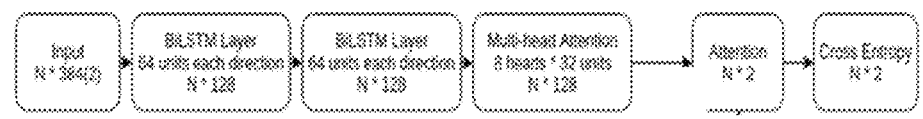

A visual and block description of the training/prediction process and flow for the first of the two RNN-LSTM-AL models used in the study (hereinafter "MODEL A" or "sequential model") is illustrated in FIGS. 5A and 5B. The inputs (mass/charge ratio intensity as a function of time) are encoded through a bi-LSTM layer and attention mechanism for relating separate positions. The prediction is performed point-wise, meaning for every input the model predicts an output. The model was trained to generate a sequence of outputs with dimensionality of N×2, where "N" is the number of input parameters (points corresponding to the retention times where an intensity value was input to the model, ranging from 50 to 300 depending on the nature of the curve in the sample, see Sec. 5.3, infra) for MODEL A, the number of data points in the sequence, and output values corresponding to each input value. The two (2) values output for each of the N points are probabilities (ranging from 0 to 1) that the corresponding point represents a peak start or a peak stop. A point, or neighborhood of points output from the model with values closest to 1 (high probability) for a given transition are then used to define a boundary for the interval over which the abundance integral (integrated over time) is computed.

The output probabilities from the model thus form distributions of boundaries. The model is trained end-to-end by gradient descent on the cross entropy loss between the predicted boundary and the ground truth, or manually-labeled peak start and speak stops. Minimum hyper-parameter search, e.g., Bayesian optimization applied to an objective function minimized with respect to the model's hyper-parameters, is applied to optimize performance on the leave-out validation or test set, in order to achieve good generalization and avoid overfitting to the training set. The featurization and hyper-parameters are discussed in more detail below.

2.4 Reference-Based Sequential Models

In some applications, due to the highly variable shape and width of transition peaks, a unified prediction model such as MODEL A may not generalize well to unseen transitions. Based on the observation that samples from different patients on the same transition are consistent in shape, a second RNN-LSTM-AL model (hereinafter "MODEL B" or "reference-based model") was also developed.

Figure 6A:
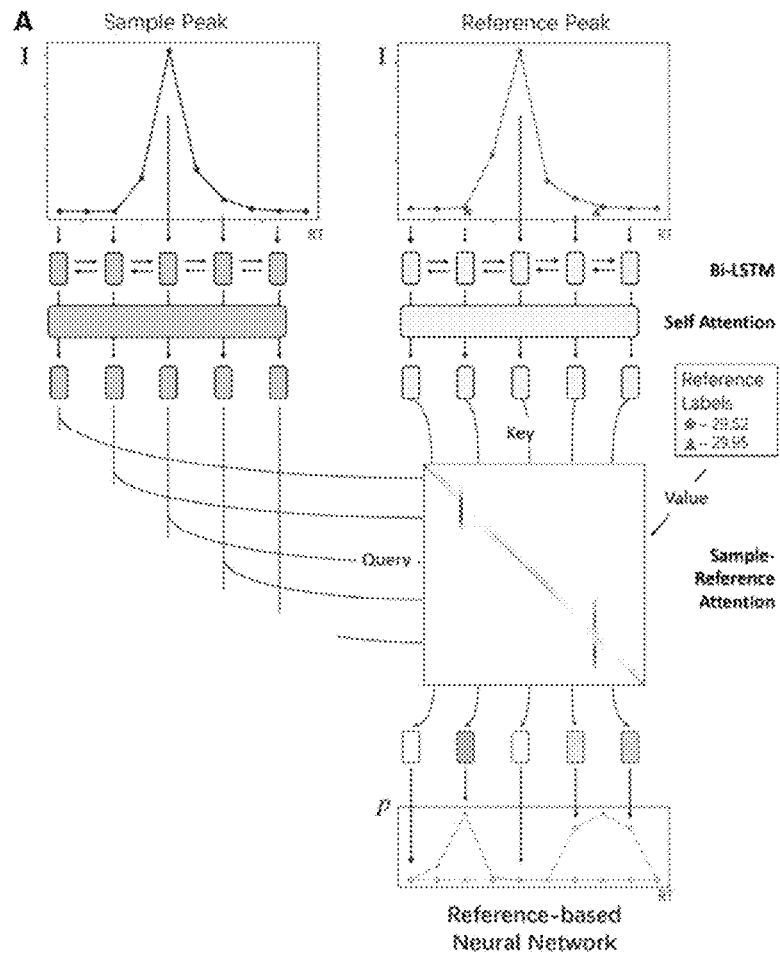
FIGS. 6A and 6B show a model architecture for a second machine learning model (MODEL B) that is a bi-directional recurrent neural network with long short term memory units and attention layer.
Figure 6B:
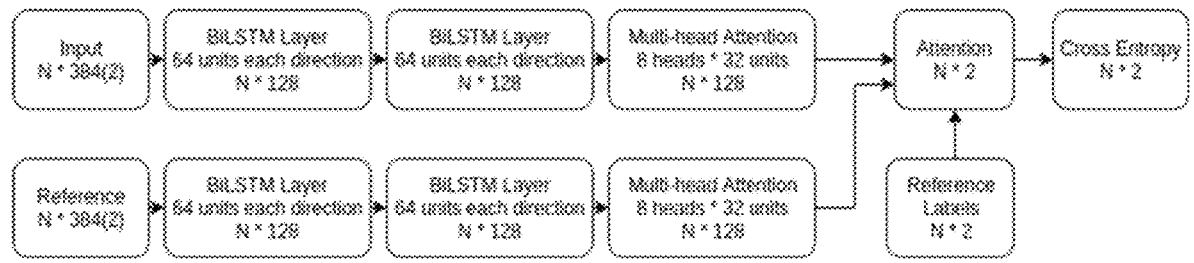
Figure 6C:
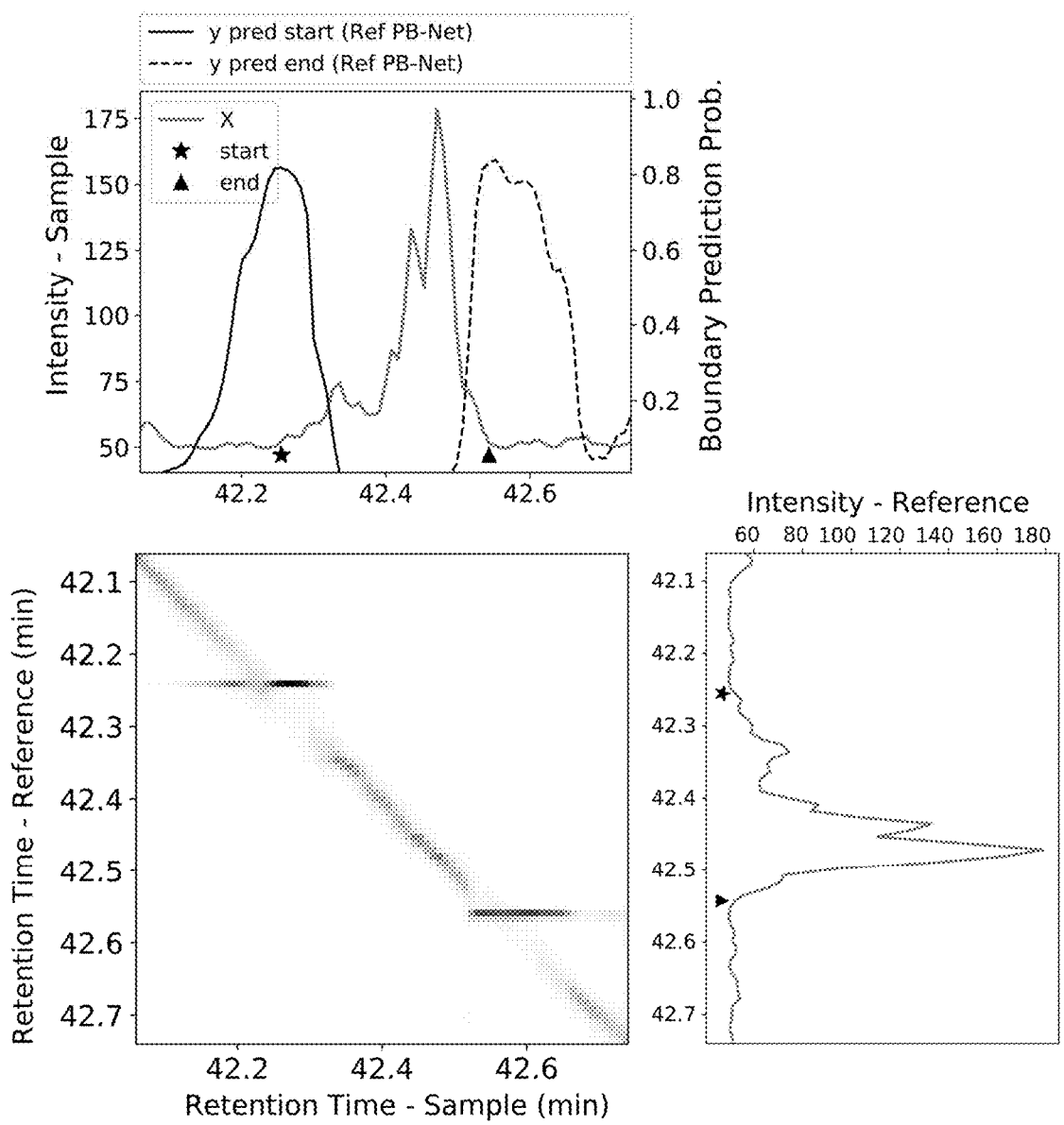
FIG. 6C shows an attention map for a sample using MODEL B.

A visual and block description of the training/prediction process and flow for MODEL B is illustrated in FIGS. 6A, 6B and 6C. MODEL B takes a query sample and reference as inputs, respectively. The encoded features for both are compared and merged in the sample-reference attention layer, generating predictions. Provided with query peak features, reference peak features and reference labels, the attention layer will compare query and reference point by point such that points in the query that are highly similar to the labeled start/end points in the reference will obtain higher predicted probabilities. Given two consistent samples, the ideal attention map of this operation will be an "identity matrix," in which points with the same surroundings are regarded as highly similar (see FIG. 6C). A divergence term between the attention map and a retention time mapping matrix was included in the optimization process to achieve good regularization.

Note that in the setting of reference-based prediction (as opposed to the query-based prediction), the task is no longer trying to identify the noise-signal transition point as with MODEL A, but rather a good encoding mechanism of a point in the sequence and its context in order to optimize the similarity mapping. In applications, reference-based models act similarly to few-shot learning models. They are trained on pairs of query/reference, aiming at accurately mapping reference labels to predictions on the query sample. This naturally allows the model to perform better on unseen transition peaks as long as a single (or a few) correctly labeled references are provided.

The adopted structure for MODEL B may be most applicable and cost-efficient for high-throughput experiments on the same set of transitions, in which manual annotations of a few high quality reference peaks are a reasonable prerequisite. On most discovery or small scale experiments a standalone reference-free predictors may be preferred.

Figure 7A:
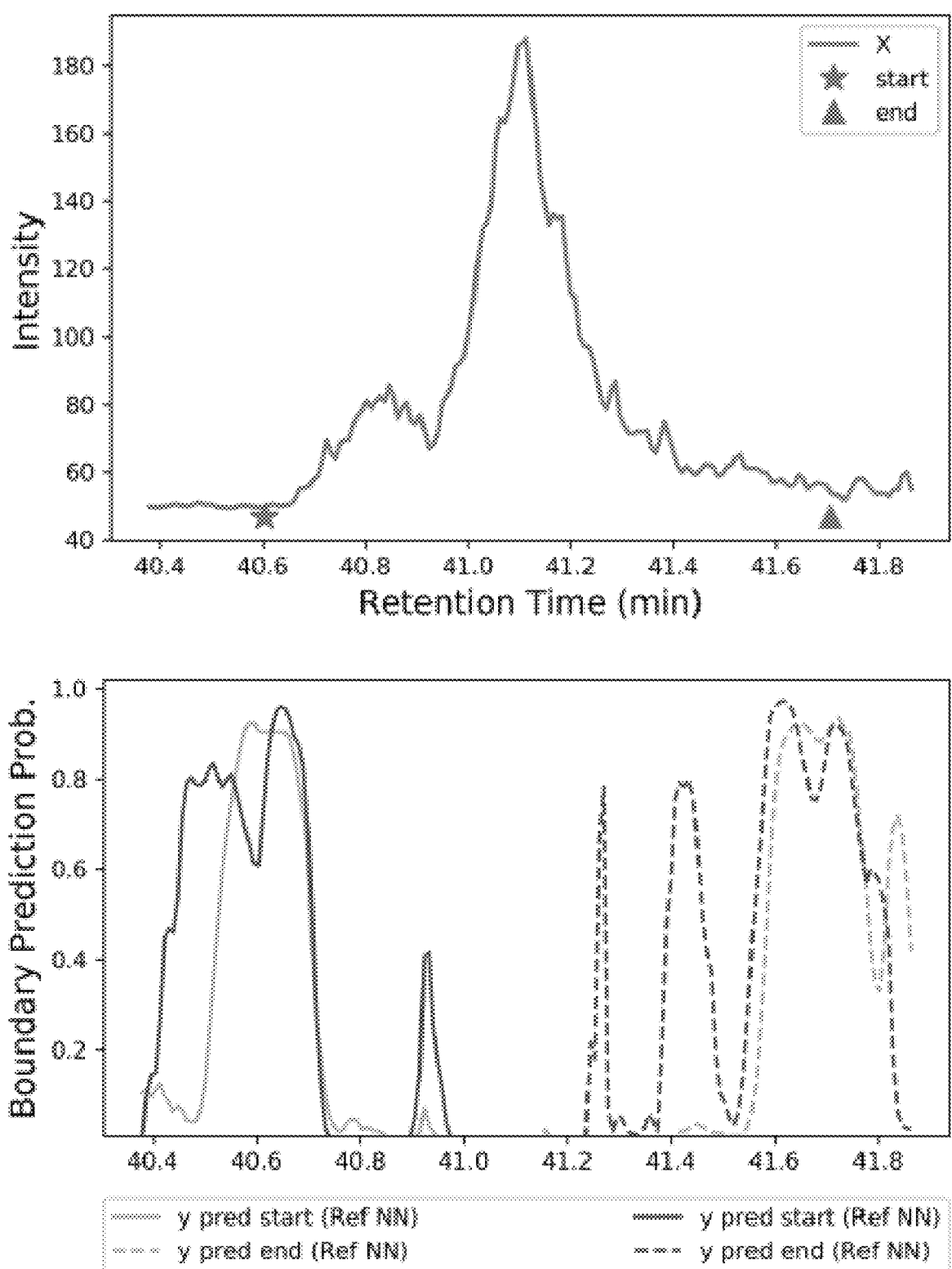
FIGS. 7A and 7B shows sample labeled input and computed probabilities (boundary predictions) for MODEL A and MODEL B, respectively. The star and triangle annotations represent labeling of MS data for training the models. The green curves represent predictions using MODEL B and the blue curve represents predictions using MODEL A.
Figure 7B:
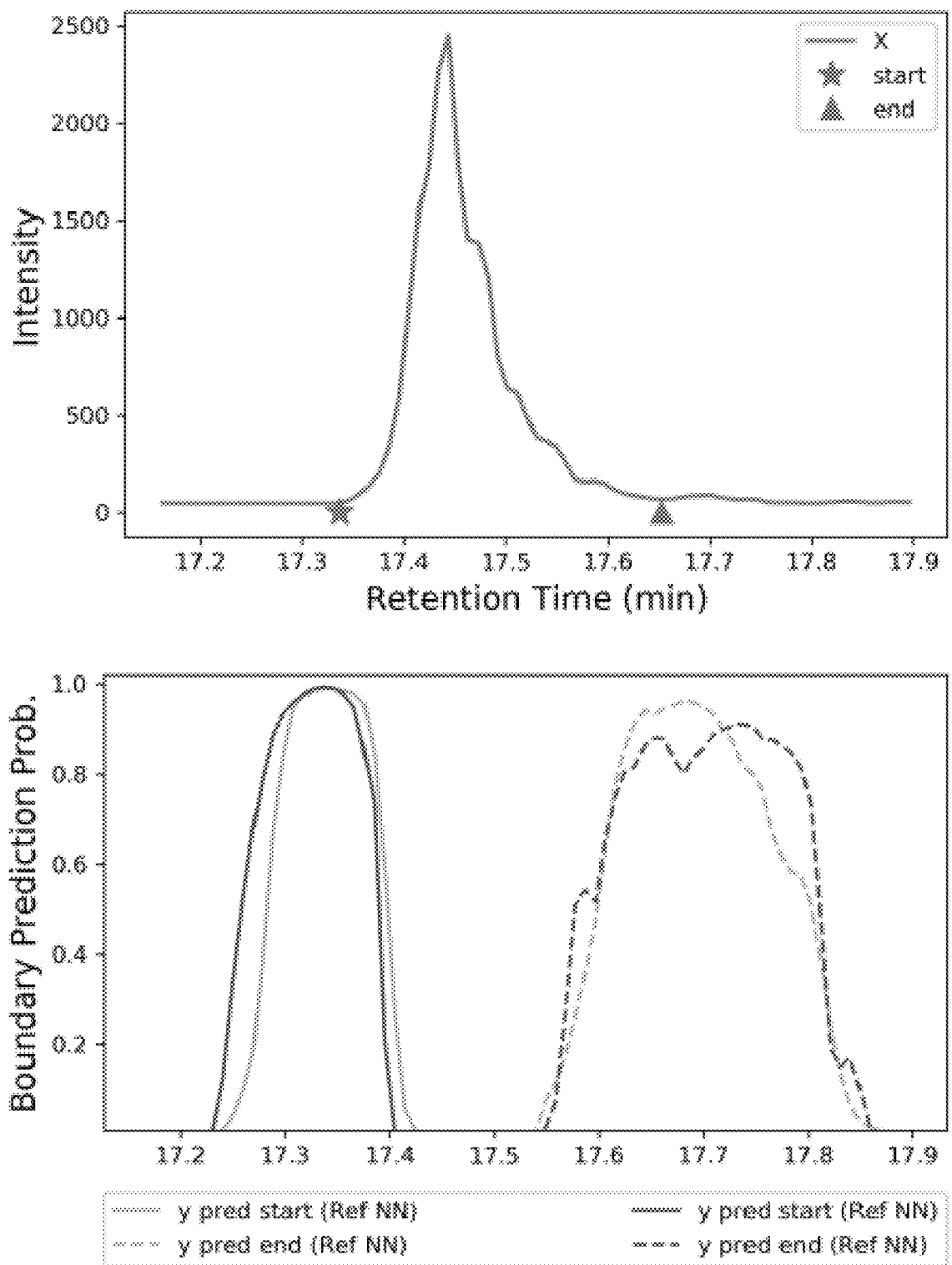

Referring to FIGS. 7A and 7B, each figure has two plots. The first plot is a plot of a transition with labeled start and stop times indicated by the star and triangle, respectively. The bottom plot is a plot of the probabilities of start/stop times predicted by the trained and validated models.

3.1 Boundary and Abundance Prediction Performance

Leave-out or test set samples were used for evaluating the models. Several metrics were used to present a comprehensive view of the problem being solved. Predictions are evaluated on two criteria: (1) accuracy in predicting boundaries (peak start/end) and (2) accuracy in predicting abundances (peak area). While the former is directly related to the setup of the problem, the latter will be of much higher importance to downstream applications which utilize analyte abundance for analysis.

In predictions, points in the curve with maximum predicted probabilities for the two tasks, i.e., the tasks of finding a peak start time and a peak end time, are used as markers for boundaries, which will be referred to as "argmax boundaries" in the following text. We calculated mean-absolute-error (MAE) between argmax boundaries and the human annotations or labels, along with an accuracy score defined as the ratio of samples whose boundary predictions are within an error threshold of 1.2 seconds (2 points in a sequence) around the ground truth annotations (human labeled points). Given that the peak duration is 20+/−8 seconds (33+/−14 points in a sequence) in the test set, the error threshold is small enough so that any boundary prediction within the window will not significantly change the abundance.

For evaluation of abundances, first calculated are baseline-adjusted integrals between boundaries from ground truths (human labeled) and model predictions respectively, and then evaluated Spearman's rank correlation coefficient (Spearman's r) and Pearson correlation coefficient (Pearson's r) between the two on each individual transition. Due to the wide range of abundances ($1 \sim 10^{15}$), Pearson's r will be dominated by samples with large abundances, here reported are correlations calculated on log-abundances instead to avoid bias. Average scores over all transitions are reported. Furthermore, for indication of practical usage, also reported is an accuracy score defined as ratio of samples whose predicted abundances are within +/−5% of the annotated abundances. Note that this accuracy metric has one caveat: integrals computed over an interval defined by boundary predictions that deviate from the annotated boundaries may appear to have very similar abundances as the annotated abundances because start/stop boundary prediction errors may cancel each other out. That is, the % error in the predicted peak start time may cancel out a corresponding % error in the predicted peak stop time when the intensity values are summed in the integral.

TABLE 1

Prediction performance on leave-out test set (67672 peaks)

| | Model Boundary Prediction | | Abundance Prediction | | |
| --- | --- | --- | --- | --- | --- |
| | MAE (second) | Accuracy* | Log-Abundance Pearson's r | Spearman's r | Accuracy** |
| Skyline | N/A | N/A | 0.6388 | 0.7372 | 0.4365 |
| Rule-based | 4.79 | 0.285 | 0.9879 | 0.9708 | 0.5847 |
| MODEL A | 2.33 | 0.432 | 0.9897 | 0.9835 | 0.6889 |
| MODEL B | 1.56 | 0.584 | 0.9974 | 0.9917 | 0.7995 |

TABLE 2

Prediction performances on train set (86311 samples)

| Model | Boundary Prediction | | Abundance Prediction | | |
|---|---|---|---|---|---|
| | MAE (second) | Accuracy* | Log-Abd Pearson's r | Spearman's Rho | Accuracy** |
| Rule-based | 3.97 | 0.311 | 0.9097 | 0.9924 | 0.645 |
| MODEL A | 1.79 | 0.601 | 0.9477 | 0.9965 | 0.743 |
| MODEL B | 1.54 | 0.667 | 0.9592 | 0.9969 | 0.779 |

\* Ratio of samples whose boundary predictions are within 1.2 seconds error
\*\* Ratio of samples whose abundance predictions are within 5% error

TABLE 3

Prediction Performances on validation set (20044 samples)

| Model | Boundary Prediction | | Abundance Prediction | | |
|---|---|---|---|---|---|
| | MAE(second) | Accuracy | Log-Abd Pearson's r | Spearman's Rho | Accuracy |
| Rule-based | 4.08 | 0.320 | 0.9141 | 0.9023 | 0.6593 |
| MODEL A | 2.57 | 0.445 | 0.9332 | 0.9270 | 0.6884 |
| MODEL B | 2.80 | 0.372 | 0.9541 | 0.9398 | 0.6563 |

Figure 8A:
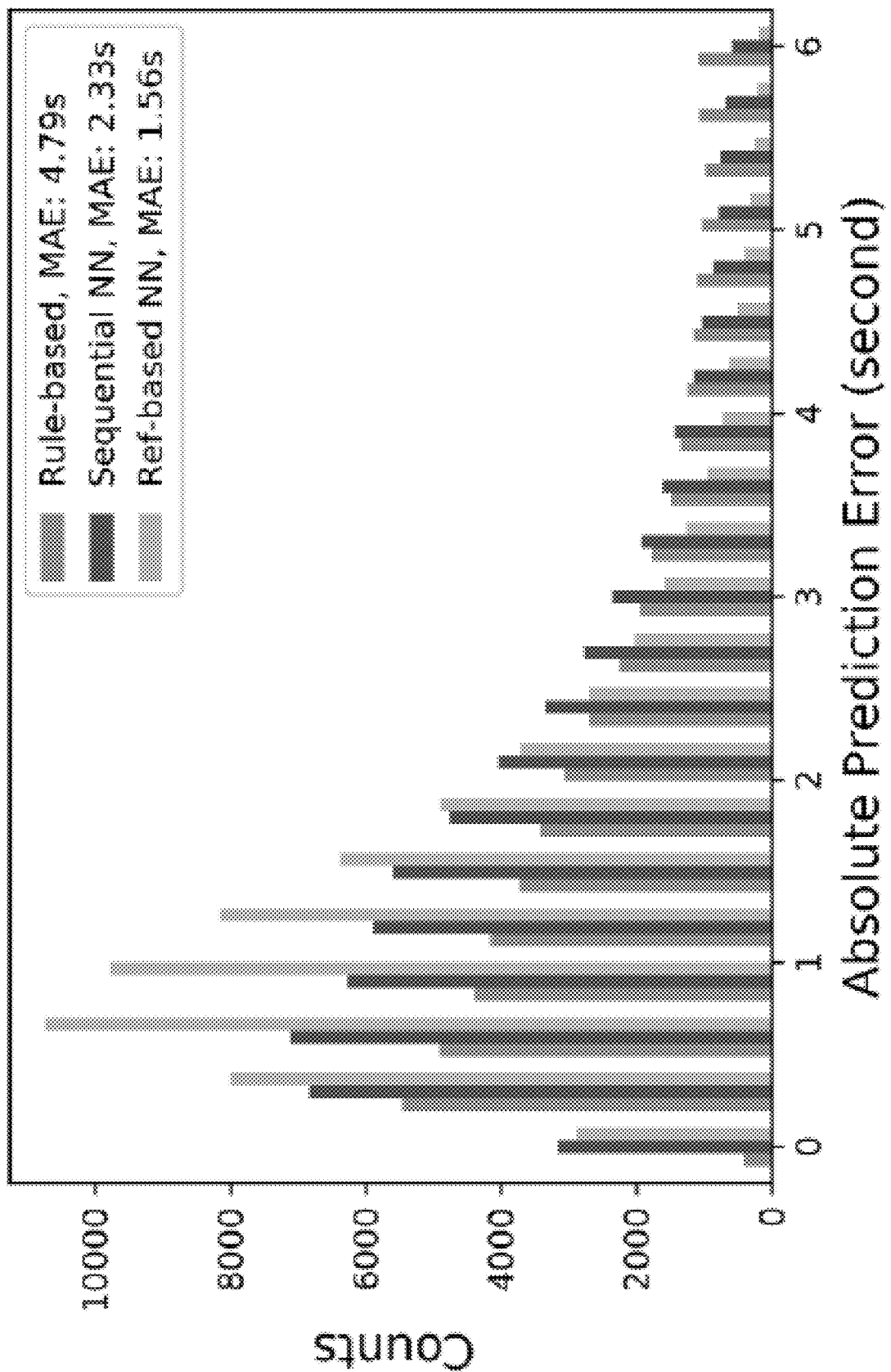
FIGS. 8A, 8B and 8C show performance of MODEL A (blue) and MODEL B (green) against a known machine learning architecture trained on same data (rule-based method—red).
Figure 8B:
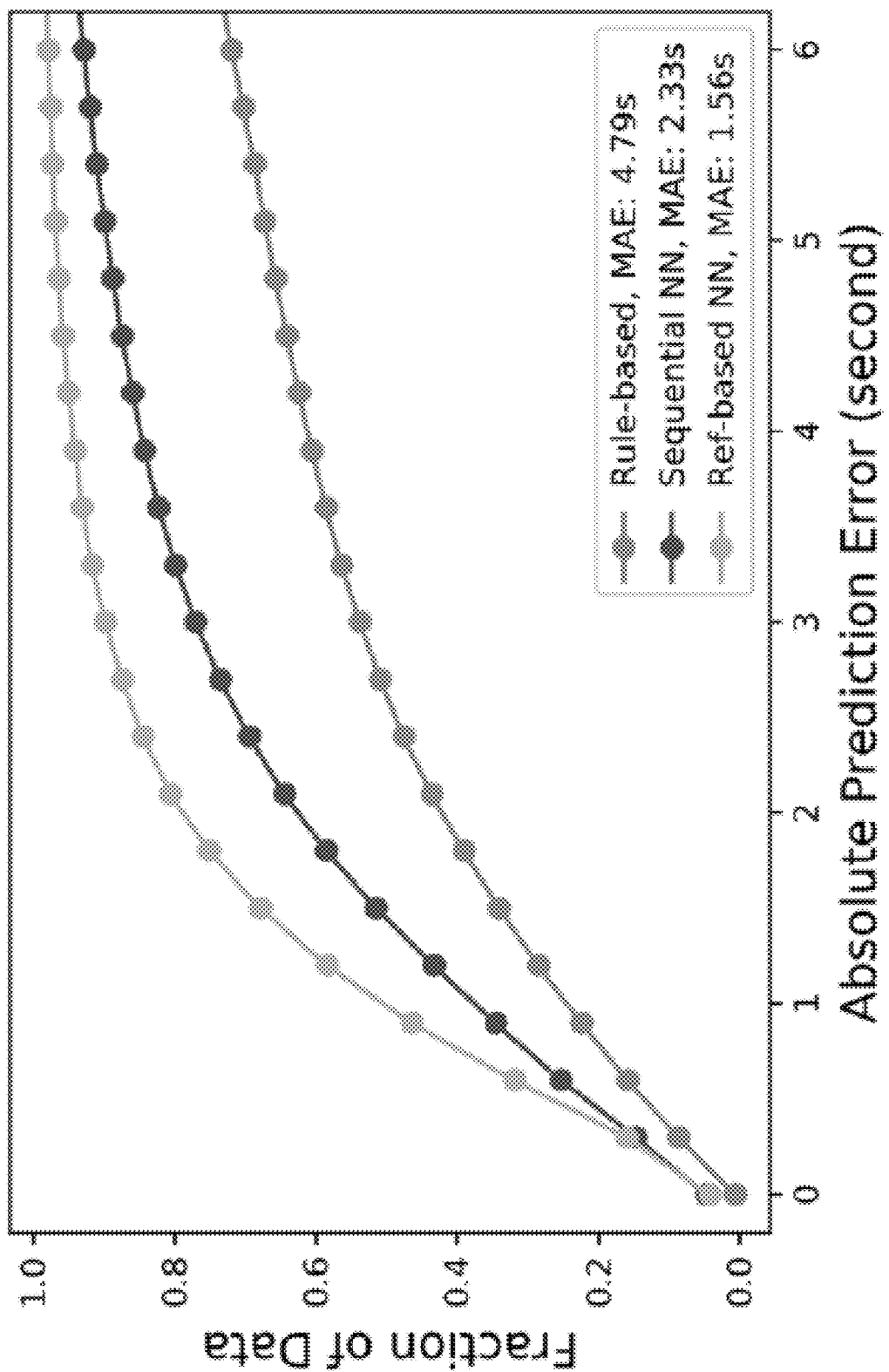

TABLE 1 presents performance scores of the three tested methods and Skyline predictions. Note that Skyline generated abundance predictions only and was not evaluated and compared on boundary prediction tasks. Both MODEL A and MODEL B demonstrated significant performance boosts on all tasks over the rule-based method and Skyline predictions. MODEL B, with the aid of extra reference data, achieved top scores. On boundary predictions, as the rule-based method is tuned to optimize training/validation set performances (see TABLE 3), strong overfitting is observed. In comparison, thanks to the better sample quality, MODELS A and B achieved MAE of 2.33 and 1.56 seconds on the test set, respectively (with and without reference), two times smaller than the rule-based method. Likewise, in accuracy score performance MODEL B took the lead with a 30% advantage over the rule-based method. FIGS. 8A and 8B show a bar plot and un-normalized cumulative distribution of boundary prediction error, respectively, in which MODELS A and B presented distributions with lower error as well as less outliers.

Abundance predictions presented similar results: MODELS A and B achieved better and more robust performances on evaluating peak abundances (FIG. 8C), with an over 20% increase on accuracy. Note that in this problem influences from errors in boundary prediction will be largely alleviated as boundary points typically contribute little to the overall integrals. Correlation scores indicated that MODELS A and B performed significantly better than current off-the-shelf mass spec data analysis software, with a near-perfect Spearman's correlation coefficient at 0.9975 and 0.9990. Intriguingly, the rule-based method also achieved much higher correlation score than the Skyline predictions. Without wishing to be tied to any theory, this result may have been due to the complex composition of test samples, which generated co-eluting peaks or compounds with close retention time. When the RT window was set closely around the desired transition (which is also a setting typically used by human annotators), Skyline might have accidentally pick peaks from different range, resulting in significantly worse performance.

Figure 8C:
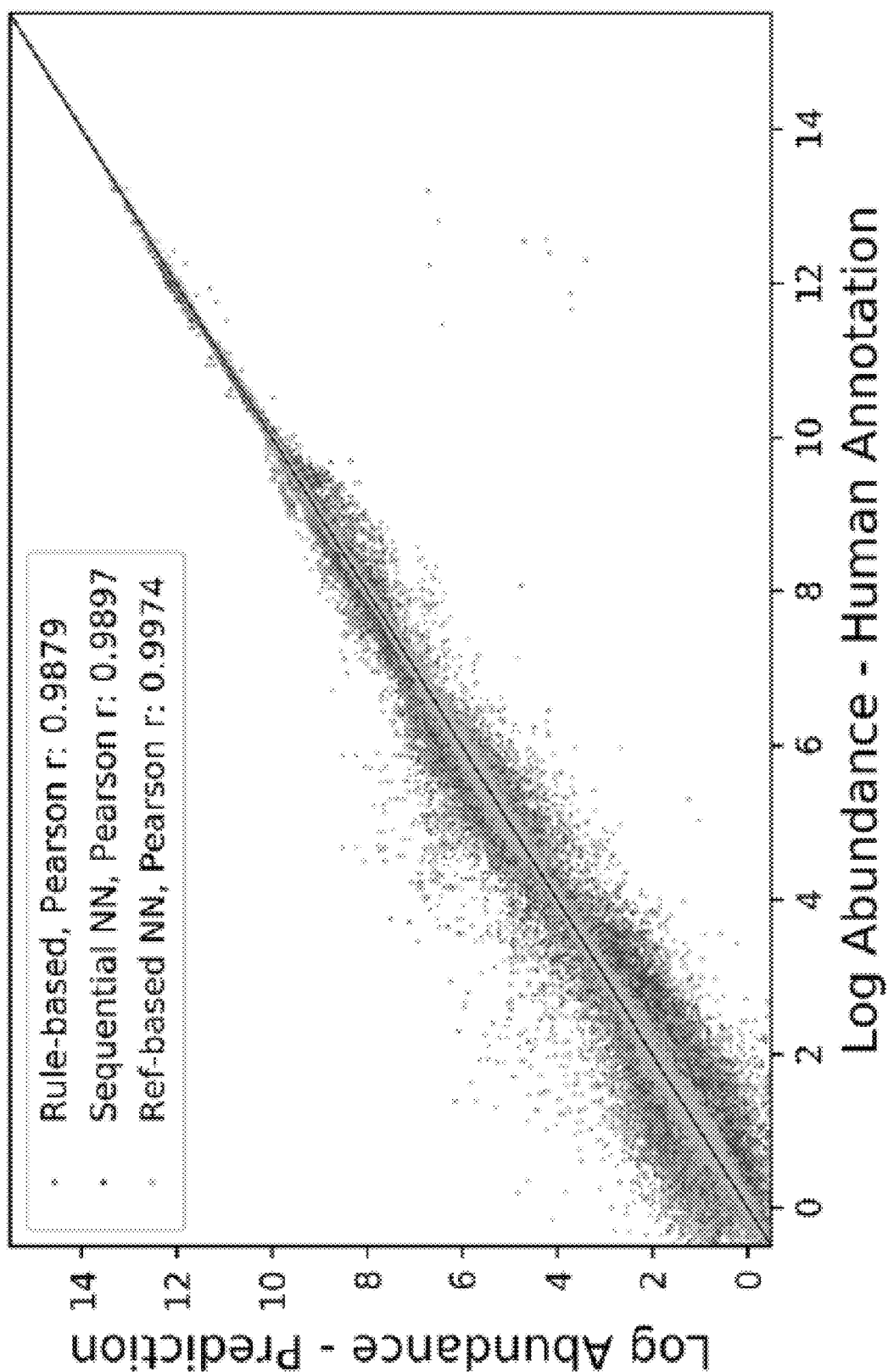

Comparing MODEL A with MODEL B, because the extra "reference data" was included during the training and validation phases for MODEL B, this model performed better than MODEL A, offering 15% and 10% increases on the accuracy of boundary and abundance predictions. MODEL B presented better boundary error distribution with fewer outliers (2.2% versus 7.1%, FIG. 8B), consistent with the observation in abundance correlation plots: green points are more concentrated around the center line while blue points include a few outlying predictions (FIG. 8C).

Depending on the application however MODEL A may be preferred, since less training sets are needed. The additional reference data used with MODEL B may not be needed, or practical for small scale applications or experiments since MODEL A may provide good accuracy/predicted abundance as the results show. MODEL B may be preferred for larger scale experiments or when more accuracy is needed.

Figure 9A:
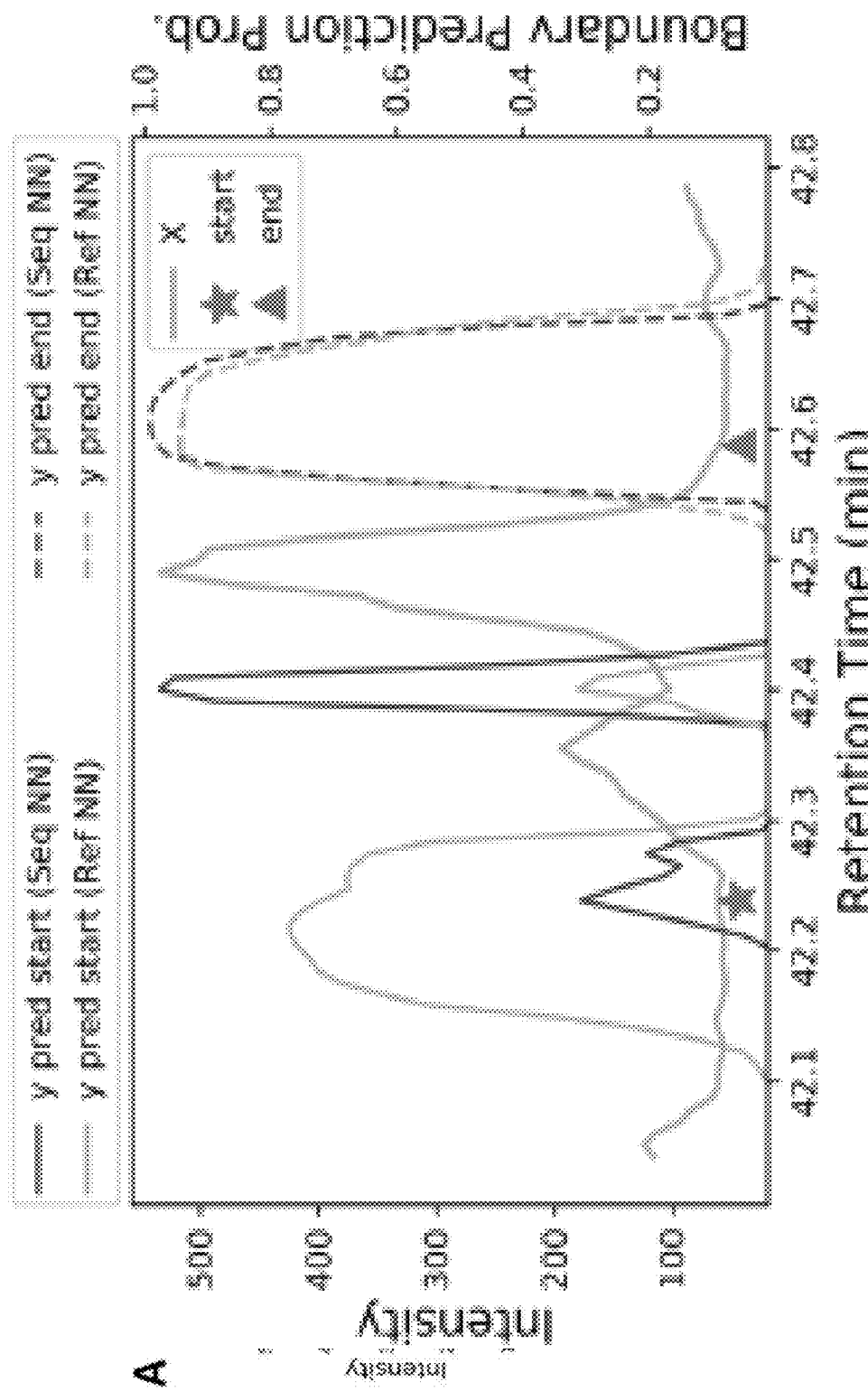
FIGS. 9A and 9B show additional sample labeled input and computed probabilities (boundary predictions) for MODEL A and MODEL B, respectively. The star and triangle annotations represent labeling of MS data for training the models. The green curves represent predictions using MODEL B and the blue curve represents predictions using MODEL A. Reference and sample peaks for a glycopeptide transition. A: In reference peak, grey line represents the input curve; red star and red triangle are human annotated peak start and end; blue/green solid line and dashed line indicate predictions from sequential/reference-based neural network model of peak start and end probabilities. B: Sample peaks for the same transition with different input curves. Note that reference-based models (green) output much more consistent predictions.

In these experiments, MODEL B provided another advantage not displayed in the plots: higher consistency in predictions on the same transitions across multiple samples. Especially for transitions whose boundaries could vary due to shoulder and valley points, the MODEL B tends to follow the same prediction form of its reference (FIG. 9A), which is the main objective of its model structure design. This is highly desirable in high throughput experiments in that abundances are generated based on the very same standard and hence allowing for more accurate comparison and quantification. But it should also be noted that the strong prior assumption in the model may also hurt its performance in cases of retention time shift or strong batch effect.

3.2 Comparison with Human Annotators

To further validate the practical usage of neural network-based models, we compared model predictions against a group of human annotators calculating peak abundances.

Within the test set, analyzed was a subset consisting of 12 transitions for all 135 serum samples, and 12 annotators marked the peak start/end independently. Combined with the original test set labels, 13 sets of human annotations are prepared for this subset. Then we calculated relative standard deviations for each sample peak across the 13 annotations as a proxy for variations between different annotators, and compared with MODEL A's and MODEL B's predictions relative errors.

Figure 10:
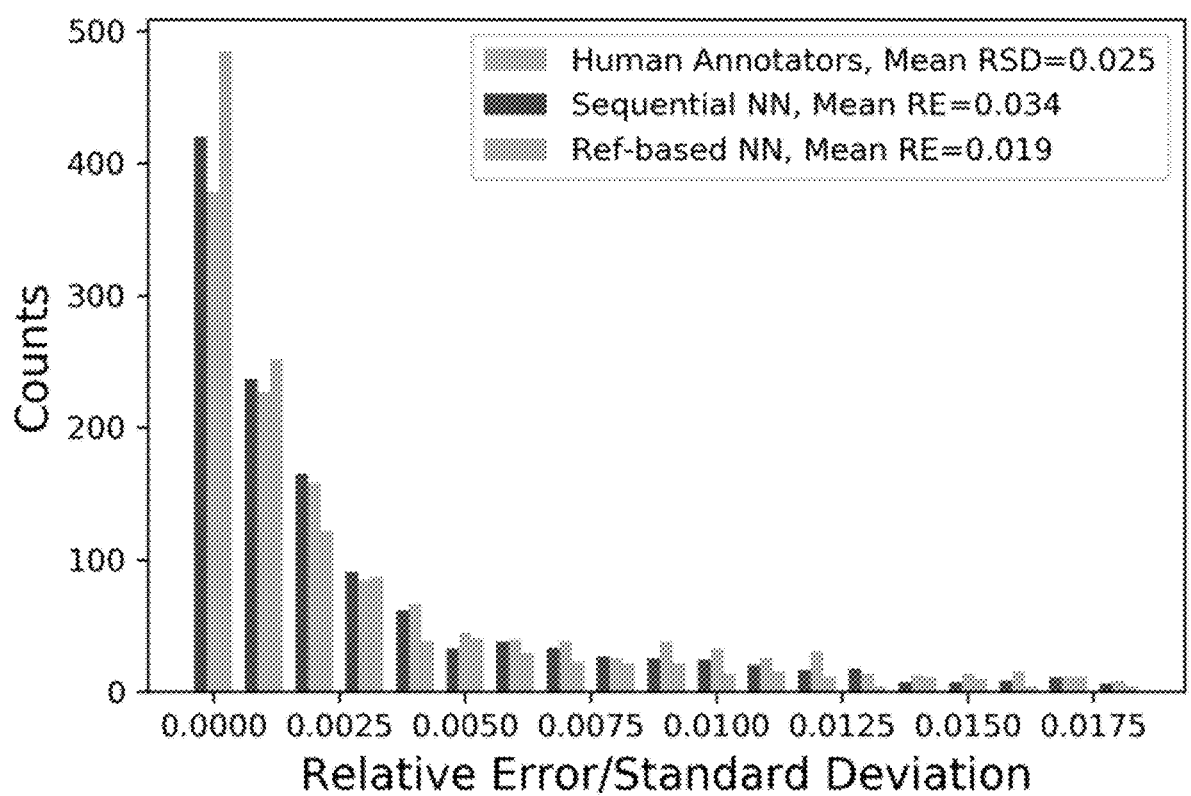
FIG. 10 relative standard deviations of boundary point selection for human annotators versus MODEL A (blue) and MODEL B (green). Bar plots are of relative standard deviations (RSD) of 13 human annotators, and relative errors (RE) of sequential/reference-based neural network predictions.

Results are summarized in FIG. 10. High consistency over annotators is observed over most samples, as demonstrated by the grey bars FIG. 10. Mean RSD over all sample peaks for human annotators is 2.5%. In parallel, both MODEL A and MODEL B performed well on the subset, achieving mean relative error of 3.5% and 2.1% respectively compared with human annotator average. The distributions of error, as shown in the blue and green bars, are similar but slightly worse than the RSD across annotators. Wilcoxon signed-rank test doesn't show significance ($p=0.11, 0.50$) for both models, indicating that the differences are not significant.

Viewing predictions from each individual annotator as a group, we then calculated pairwise differences between annotators: average of the relative abundance differences on each sample peak. The outcomes show a discrepancy between annotators at 0.025+/−0.009, in line with the RSD value. At the same time, difference between the MODEL B prediction and the 13 annotators is 0.026+/−0.007, overlapping with the inter-annotator difference. Corresponding value for MODEL A is 0.039+/−0.005. Given that the model vs. human difference is not significantly larger, or even close in the reference-based case, it is clear that the neural network-based models can serve as good substitutes for manual annotations in this task. We also note that the human annotators had a peak with selected start and stop to serve as a reference for their reads, making their task directly analogous to the MODEL B.

3.3 Weighted Peak Start/End for Abundance Calculation}

Figure 9B:
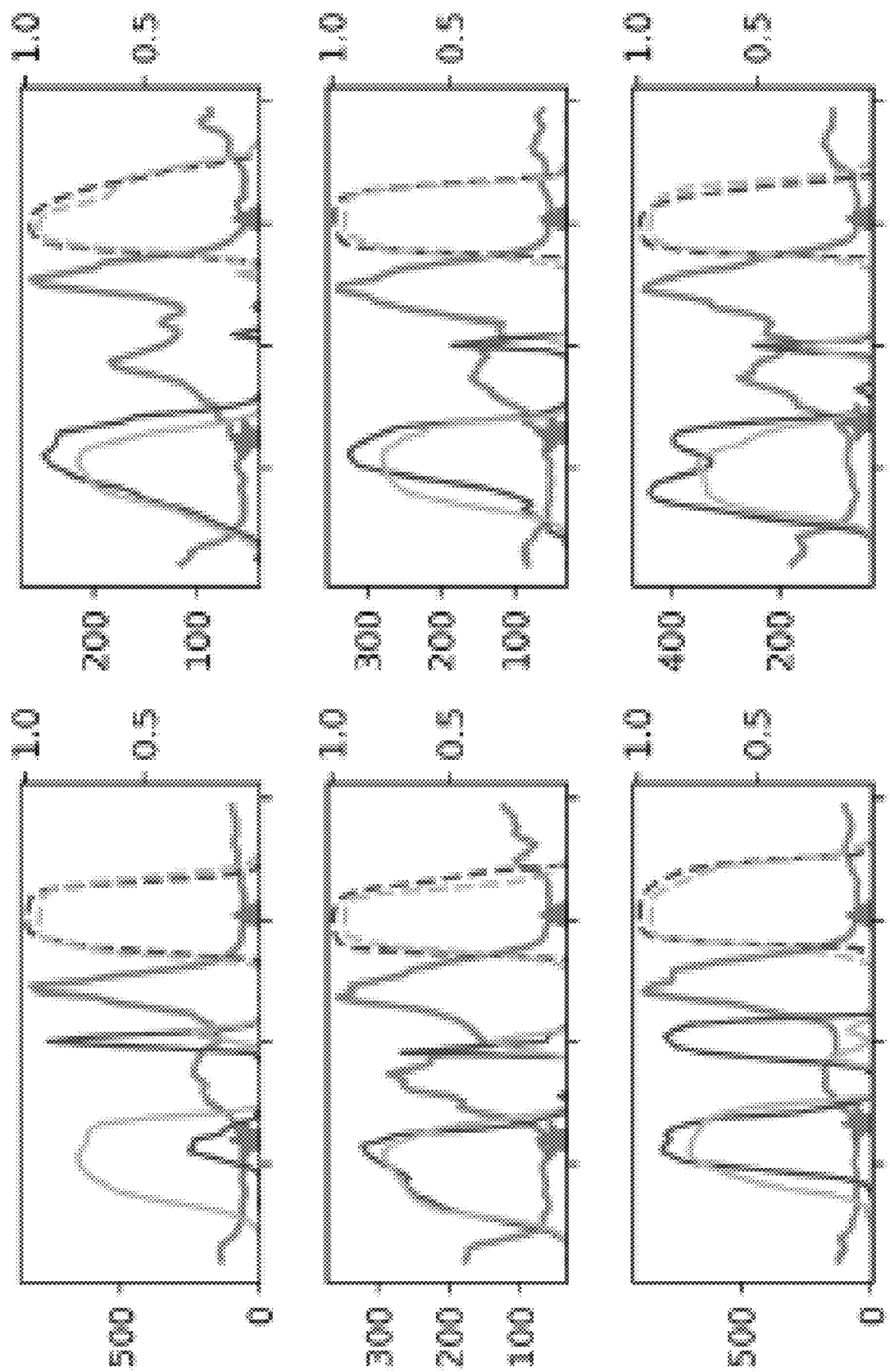

In peaks with shoulder and valley points, determination of boundaries will suffer from a much higher variability. Even in human annotations variations across different annotators exist, so it is expected that output from MODEL A and MODEL B will present multimodal shapes due to the averaging over the ensemble of training samples (FIG. 9B, FIG. 7B). This is rather severe in reference-free cases (MODEL A) as there doesn't exist a strong reference prior, causing results to sometimes be arbitrary when applying the argmax boundaries. In these cases methods were reviewed that can better accommodate full predictions instead of a single point estimate of boundaries.

One of the most direct ways is to interpret the prediction outcomes as probability distributions. In other words, to have the model evaluate probabilities of all possible pairs of points in a sequence that could serve as peak start/end markers. For a sequence of N points, this involves in total N×(N−1)/2 pairs after imposing the order constraint. Each pair's probability can be easily calculated by multiplying the prediction values of the peak start/end tasks on the two points. The probabilities are then used to calculate the weighted sum over the integrals between corresponding pairs, providing a mean estimate instead of a MAP estimate (this alternative method for computing abundances will hereinafter be referred to as the "weighted sum method"). A MAP estimate computes one abundance value using the argmax values as endpoints.

Figure 11A:
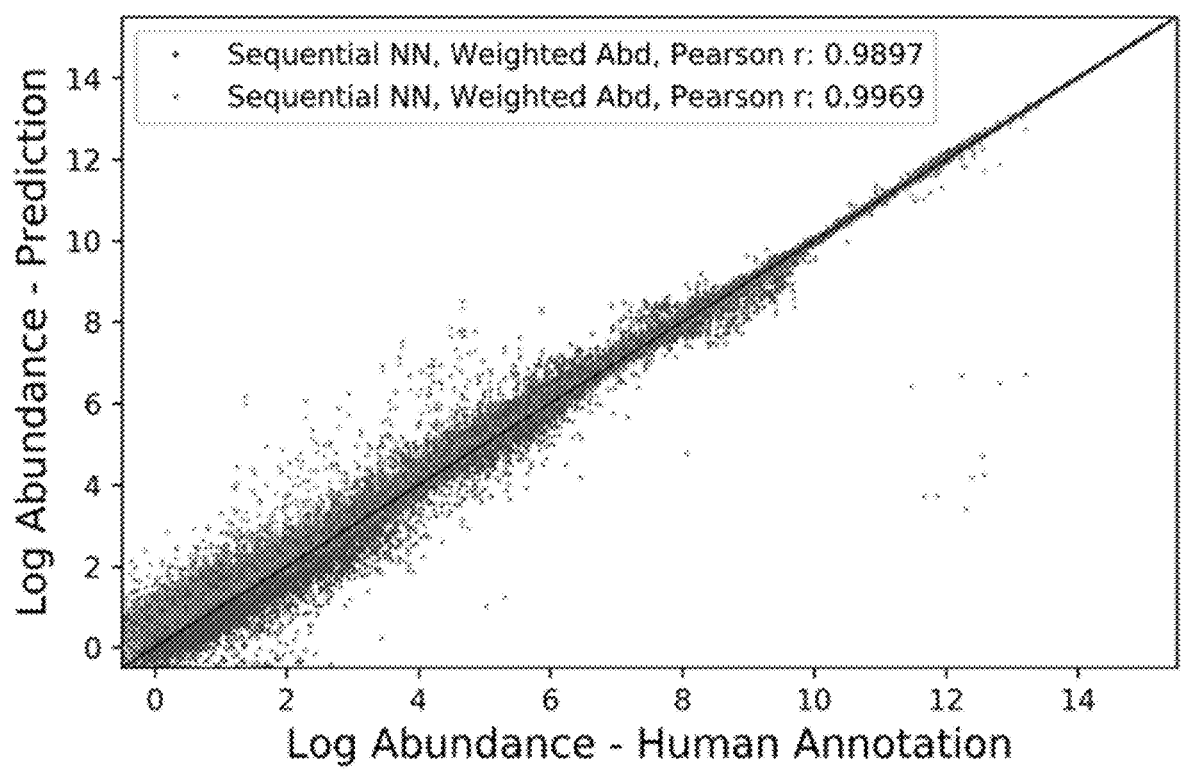
Figure 11B:
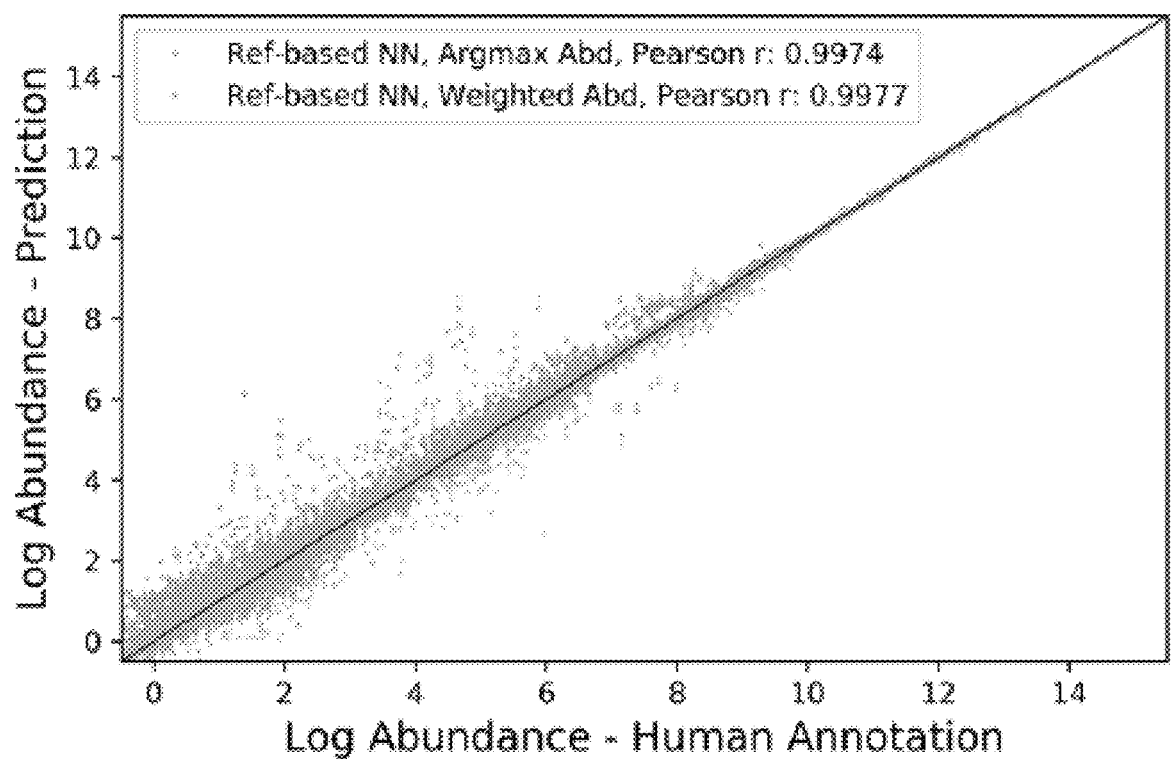

A mean of the abundances may provide more robust abundance estimates than using argmax boundaries, especially when a model architecture more similar to MODEL A than MODEL B is used. As no explicit boundaries are used, the method may avoid issue of peak end prediction appearing prior (or very close) to a peak start prediction. A comparison of abundance correlation for MODEL A and MODEL B is presented in FIGS. 11A and 11B, respectively.

Especially for MODEL A, the weighted sum method helped in generating more accurate abundances, raising abundance correlation from 0.9897 to 0.9969. Increase in MODEL B is relatively minor (from 0.9974 to 0.9977). The post-processing step mainly helped in avoiding outliers whose argmax boundaries caused significantly lower abundances than human annotations. These samples typically suffer from abnormally high predicted boundary probabilities within the range of peak (at valley or shoulder points), which are then chosen by the argmax operation. At the same time, the weighted sum method caused overall predictions to bias upwards for low-abundance peaks, which is mainly due to noisy signals and predictions. In cases where signal-noise ratio is low, predicted boundary probability could fluctuate on a longer retention time range at the periphery of a peak (FIGS. 7A and 7B, and FIG. 12), leading to a higher weighted sum. We deemed this effect to be acceptable as noisy peaks will be of less value for downstream applications.

From these rules, confidence values were calculated as follows: for prediction on a sample curve with N points, calculate all local maximums in the range. The global maximum is labeled as $(\hat{x}^*, \hat{y}^*)$, in which $\hat{x}^* \in \{1, 2, \ldots, N\}$, $\hat{y}^* \in [0, 1]$.

Local maximums (if they exist) on its left are labeled as $(\hat{x}_i, \hat{y}_i)$, i=1, 2, ..., p, in which $\hat{x}_1 < \hat{x}_2 < \ldots < \hat{x}_p$, local maximums on the right (if they exist) labeled as $(\tilde{x}_j, \tilde{y}_j)$, j=1, 2, ..., q, in which $\tilde{x}_1 > \tilde{x}_2 > \ldots > \tilde{x}_q$. By further defining $\hat{x}_0 = \hat{x}^*$ and $\tilde{x}_0 = \hat{x}^*$ the confidence is calculated as:

$$\text{Confidence} = \hat{y}^* - \frac{1}{N-1}\left(\sum_{i=1}^{p}(\hat{x}_i - \hat{x}_{i-1}) \times \max(\hat{y}_i, \hat{y}_{i+1}, \ldots, \hat{y}_p) + \sum_{j=1}^{q}(\tilde{x}_{j-1} - \tilde{x}_j) \times \max(\tilde{y}_j, \tilde{y}_{j+1}, \ldots, \tilde{y}_q)\right)$$

Figure 12:
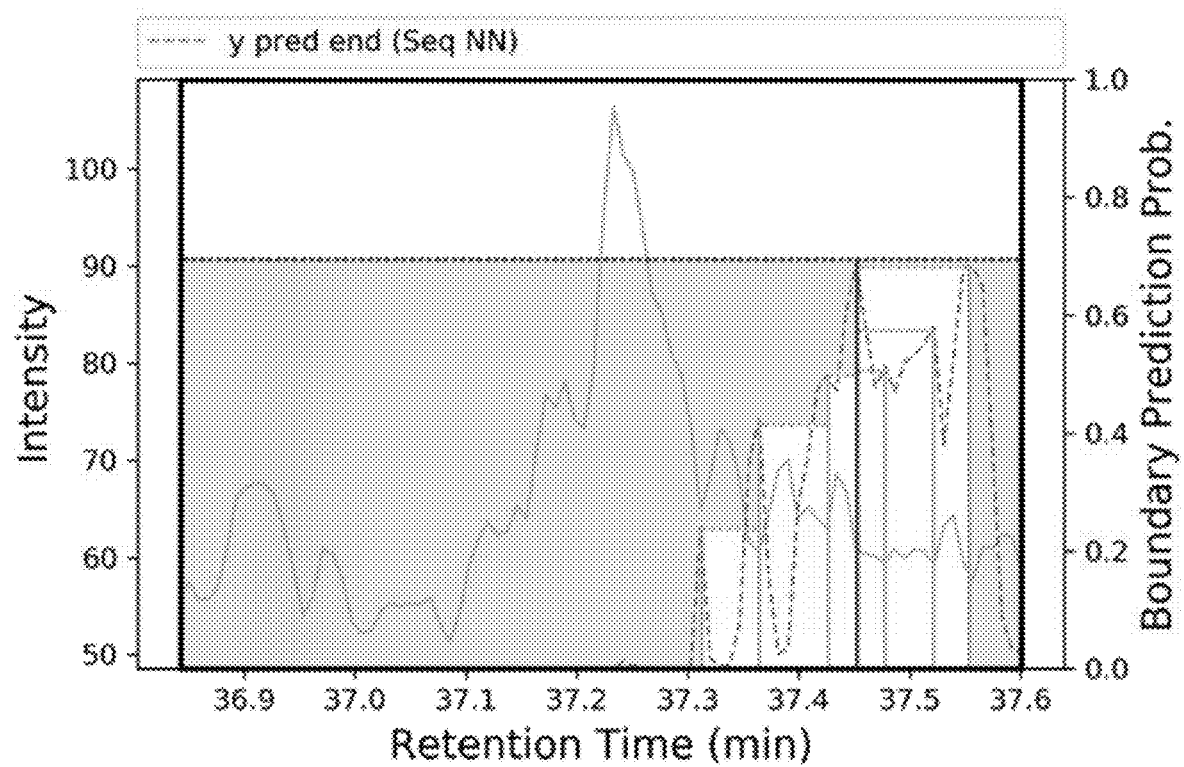
FIG. 12 shows confidence scores for MODEL B and equation used to compute confidence score. Illustration of confidence score: blue dashed line—model predicted peak end probability; dark red line—argmax prediction; light red lines—other local maximums. Confidence score (0.634) is the area of shaded area divided by the area in the black box.

A graphic illustration is shown in FIG. 12.

3.4 Prediction Confidence

Another core advantage of the point-wise prediction structure is ease in estimating prediction certainty. Though internal ways of quantifying uncertainty in neural network predictions are still complex and come with restrictions, it is fairly straightforward in this task to infer certain/uncertain by inspecting model predictions for boundaries. Most predicted probabilities will take the form of Gaussian mixtures, the quantity and heights of which represent the model's confidence. In the study a heuristic method was adopted to quantify prediction confidences based on the guidelines below:

item Lower predicted values→lower confidence;
item Multiple local maximums→lower confidence;
item More dispersed local maximums→lower confidences.

From these rules, confidence values were computed. FIG. 12 provides a description of the math used to compute the confidence level, along with a graphical illustration. The confidence score is proportional to the shaded area. One wants the prediction values to be high (close to 1) and unimodal, or close if multiple local maximums appear.

Figure 13A:
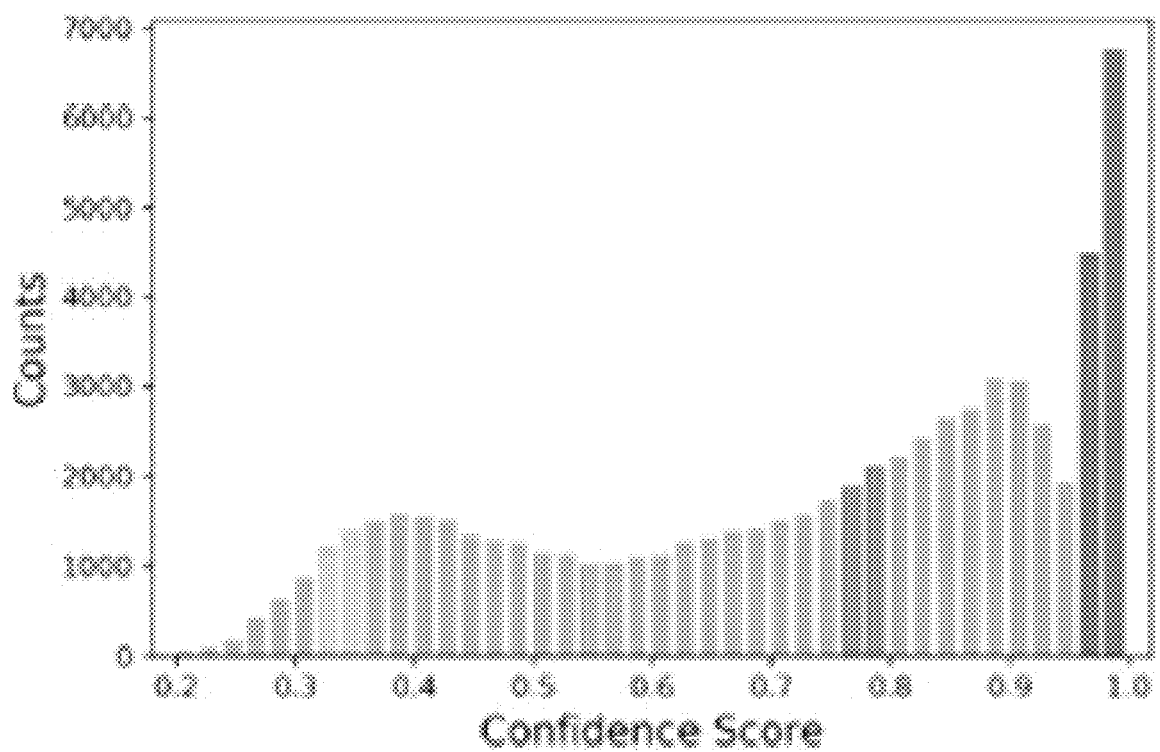
FIG. 13A shows: Histogram of prediction confidences from sequential neural net-work. Abundance predictions of samples from four bins are illustrated in the following panels.
Figure 13B:
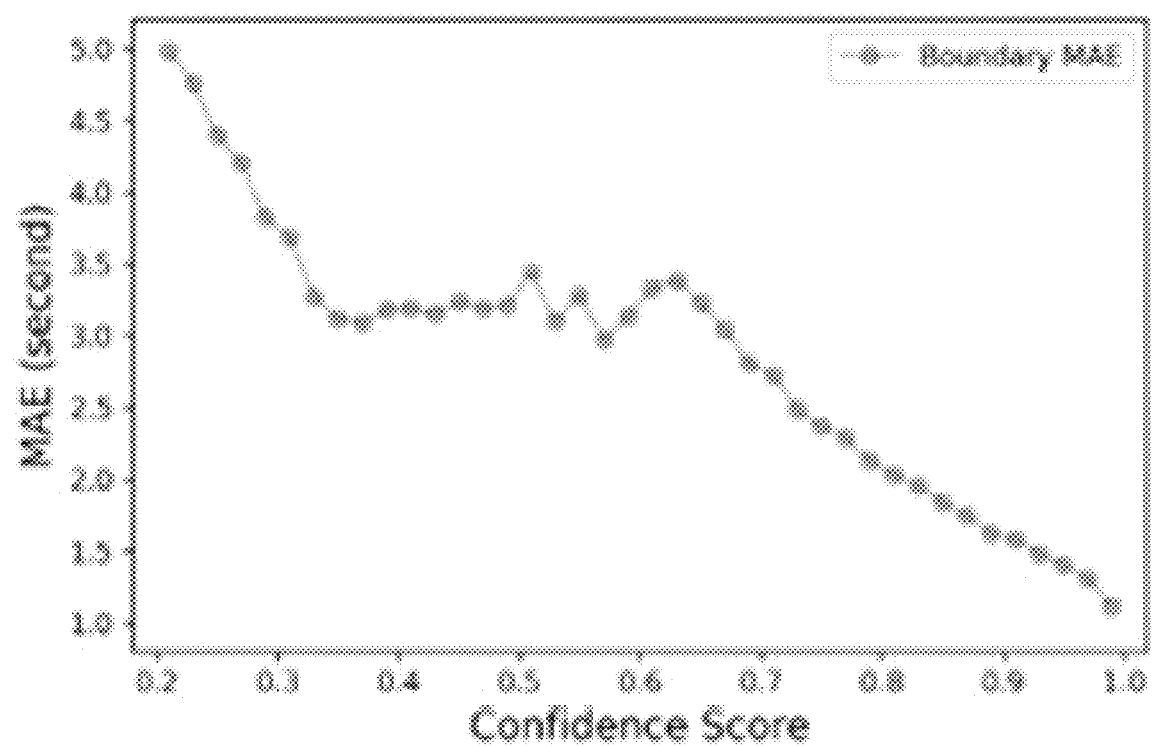
FIG. 13B shows: Mean-absolute-error (MAE) of boundary predictions decreases steadily on samples with higher confidence.
Figure 13C:
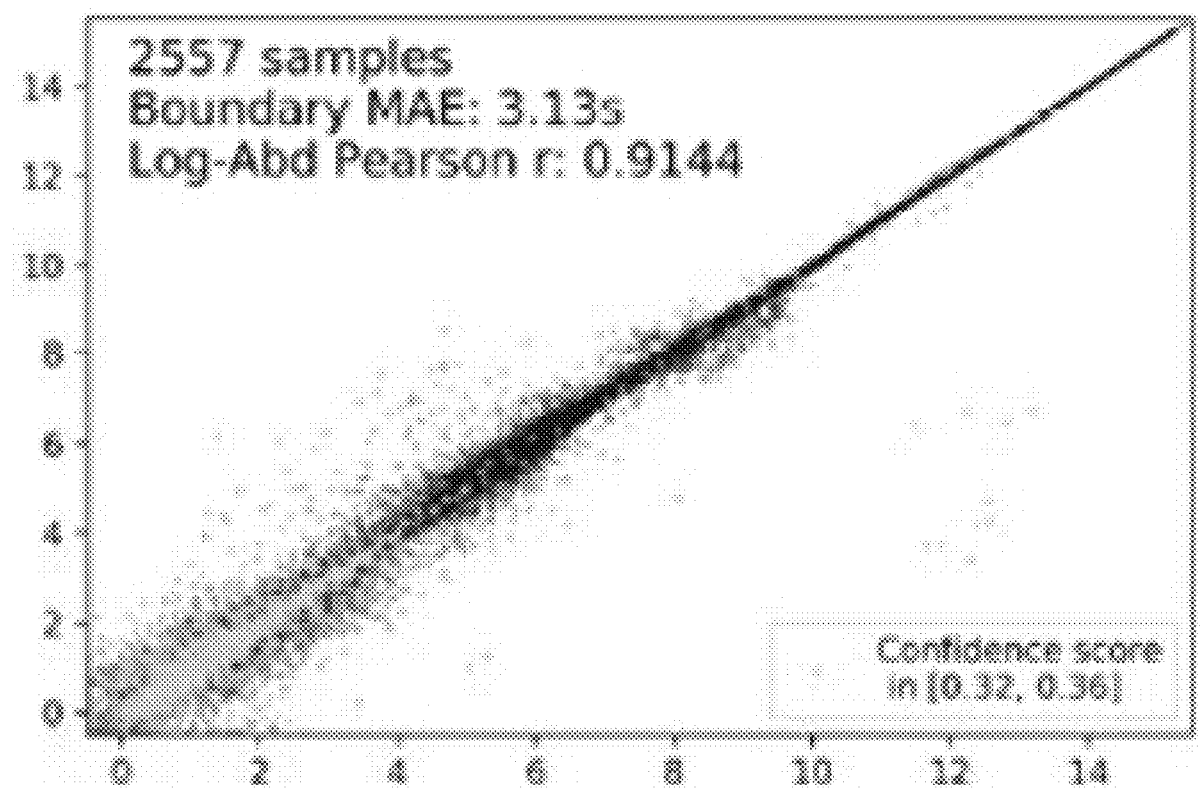
FIG. 13C, FIG. 13D, FIG. 13E, and FIG. 13F show: Scatter plots of peak abundance prediction/annotation in different confidence score bins. Samples with higher confidence achieved better correlation scores. Note that reported log-abundance Pearson's r values are calculated on the combination of samples from different transitions.
Figure 13D:
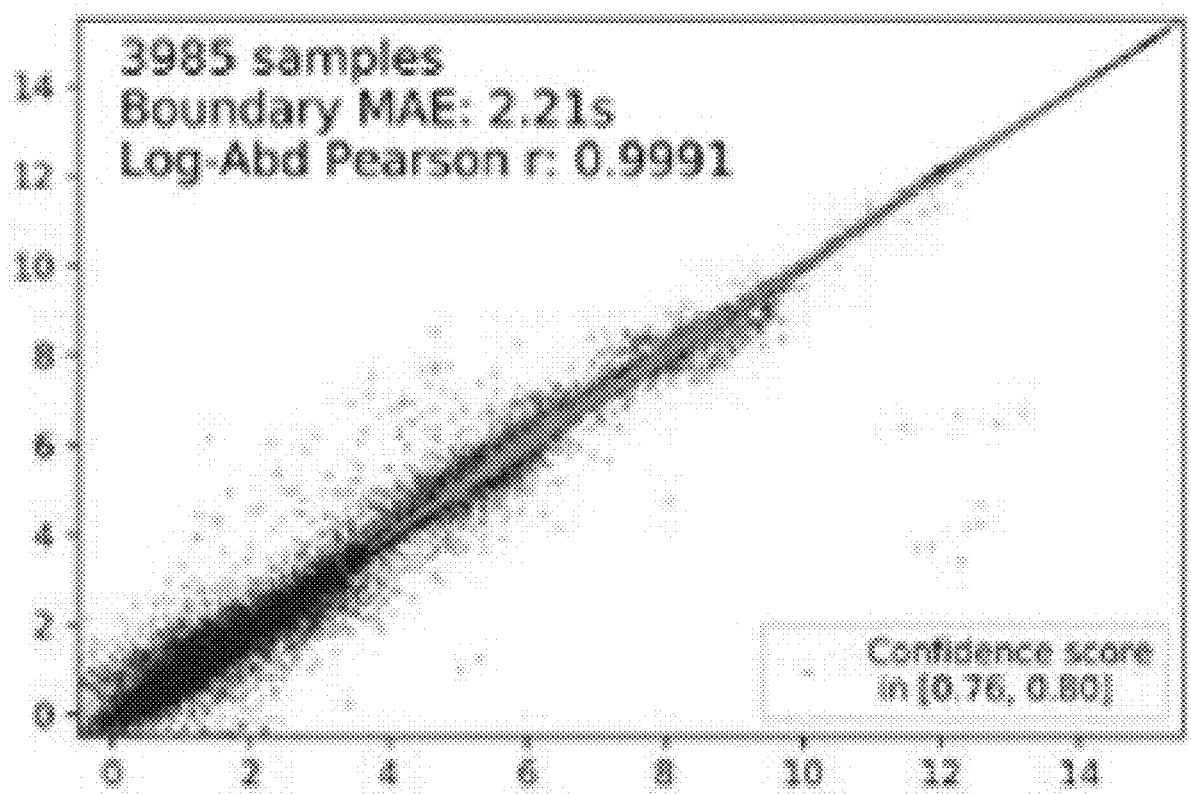
Figure 13E:
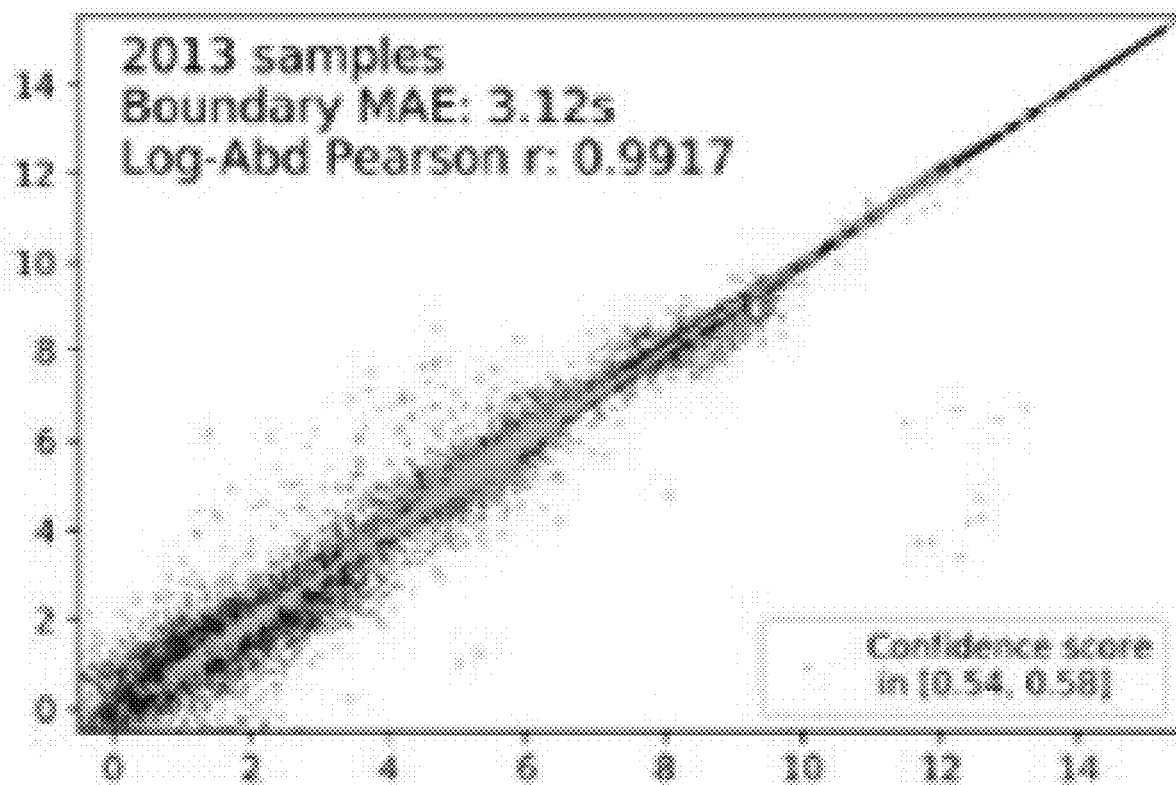
Figure 13F:
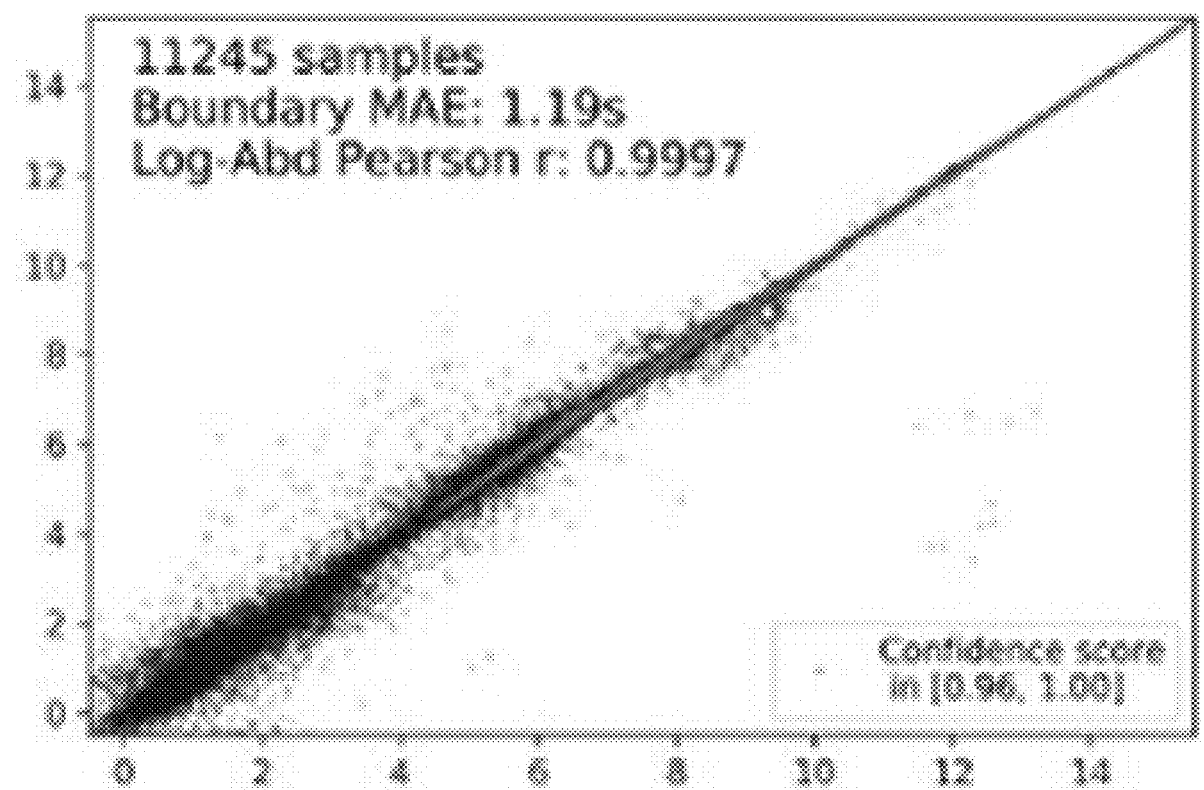
Figure 14A:
FIG. 14A shows: Histogram of prediction confidences from reference-based neural network.
Figure 14B:
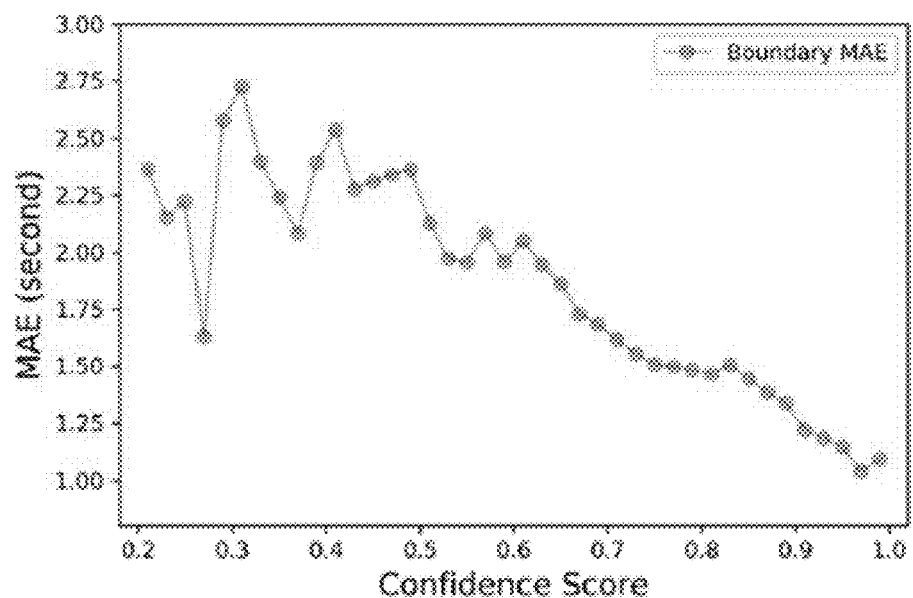
FIG. 14B shows: Mean-absolute-error (MAE) of boundary predictions decreases steadily on samples with higher confidence.

Confidence scores were computed for all predictions for MODEL A and MODEL B (FIGS. 13A and 14A). Across different confidence cutoffs, one can see a trend of performance change. As shown in FIGS. 13B and 14B prediction errors on boundaries steadily decrease with increasing confidence, dropping to near 1 second on the most confident samples.

Correlation of abundances on different confidence intervals are illustrated in FIGS. 13A-13F. Predictions on high-abundance samples typically have higher confidence and align better with human annotations. The top two bins predictions achieved Pearson's rover 0.999. In contrast, samples with lower prediction confidence yield worse performance, with higher boundary mean absolute errors (MAEs) and lower abundance correlations. This is in part due to the worse signal-noise ratio of input samples as indicated by the low abundances. Overall, the measurement of confidence served as a good indicator of noise scale and model performance.

This post-processing step may provide versatility in implementing workflow quality control. In real world applications, a direct usage would be setting up a threshold confidence score such that predictions below the value should be excluded or presented to human experts for reevaluation. This would also be helpful for detecting abnormalities in experimental data.

5.0 Experimental
Experimental Parameters

Chemicals and Reagents: Human serum, dithiothreitol (DTT) and iodoacetamide (IAA) were purchased from Sigma-Aldrich (St. Louis, MO). Sequencing grade trypsin was purchased from Promega (Madison, WI). Acetonitrile (LC-MS grade) was purchased from Honeywell (Muskegon, MI).

Sample Preparation: Serum samples were reduced with DTT and alkylated with IAA followed by digestion with trypsin in a water bath at 37 C for 18 hours. To quench the digestion, formic acid was added to each sample after incubation to a final concentration of 1% (v/v).

5.1 LC-MS Analysis

Digested serum samples were injected into an Agilent 6490 triple quadrupole mass spectrometer equipped with an Agilent 1290 infinity UHPLC system and an Agilent ZORBAX Eclipse Plus C18 column (2.1 mm×150 mm i.d., 1.8 μm particle size). Separation of the peptides and glycopeptides was performed using a 70-min binary gradient. The aqueous mobile phase A was 3% acetonitrile, 0.1% formic acid in water (v/v), and the organic mobile phase B was 90% acetonitrile 0.1% formic acid in water (v/v). The flow rate was set at 0.5 mL/min. Electrospray ionization (ESI) was used as the ionization source and was operated in positive ion mode. The triple quadrupole was operated in dynamic multiple reaction monitoring (dMRM) mode. The peptide and glycopeptide transitions employed in training and testing were a selection of those published in Li, et al., Site-Specific Glycosylation Quantification of 50 serum Glycoproteins Enhanced by Predictive Glycopeptidomics for Improved Disease Biomarker Discovery, *Anal. Chem.* 2019, 91, 5433-5445; DOI. 10.1021/acs.analchem.9b00776, the entire contents of which are herein incorporated by reference in its entirety for all purposes.

5.2 Dataset Preparation

Training and validation set peaks and test set peaks were collected from two sets of mass spectra experiments. Set one consisted of human serum samples and transitions measured in Carlito Lebrilla's lab at UC Davis in late 2017, while set two were commercially-available serum from ovarian cancer and benign mass patients purchased from Indivumed GmbH in mid-2018. Both sets of samples underwent the experimental protocol outlined above. Post-run, Agilent.D format files were converted to mzML via msConvert within the Proteowizard 3.0 software suite for bioinformatic processing.

To obtain human annotations, all transitions were labeled by a mass spectra specialist for one reference serum sample (pooled Sigma serum), and these labels make up the "reference" peaks. For the remaining samples, an annotator labeled the peak start and peak end retention time marks in Agilent MassHunter Quantitative Analysis B.5.0, based on the reference peak and accounting for any shift in retention time.

From the two experiments, only peaks labelled with positive abundances were selected. Samples with large retention time shift (>0.2 min) were also excluded. In total 106355 (train/validation) and 67672 (test) peaks passed sanity tests and were used in this study. For each transition, we collected all signals within a retention time window from reference retention time start−0.2 minutes to reference retention time stop+0.2 minutes, allowing for a mass-charge ratio window of +/−0.1 around the desired precursor and product m/z. Signals were summed along the mass-charge ratio window, producing an extracted-ion chromatogram (XIC). Both sequential models and human annotators are presented with the XIC curves cropped around the target transition (FIGS. 7A, 7B and 9B show some example XIC inputs).

The test set used in the above section entitled "Comparison with human annotators" contained 1619 peaks. All peaks were further annotated by 12 annotators independently for consistency, but only annotations with positive abundance were used to calculate transition-wise relative standard deviation and pair-wise discrepancies between annotators.

5.3 Featurization

Inputs are formulated as sequences of points on the intensity-retention time plane, with no fixed start/stop or length. To generate a uniform representation, featurization was applied on each sample curve. Retention times for all points in a single sample were first centered at the sample curve's apex position, then expanded by 128 equally spaced Gaussian bins, ranging from −1 min to 1 min, generating a vector $F_{RT}$ of 256 real numbers representing time points.

Mass to charge intensity values have a wide range, intensity values were similarly discretized by applying 256 Gaussian functions on the range from 0 to 500, turning the analog values into a vector $I_{RT}$ of 256 real values representing intensity. Adopting the assumption that any points with intensities larger than the top threshold should be regarded as part of a peak, only those points located in noise or noise-signal transition stages were featurized. The full input X for each sample curve (i.e., input parameters or states to the RNN model) after forming $F_{RT}$ and $I_{RT}$ was formed is matrix of size N×384. The variable N ranged from 50 to 300, representing the length of the curve.

For MODEL B, each sample is paired with its reference. The pair of inputs will have the same featurization process as above and were formed as two matrices X and $X_{ref}$ of dimensions N×384 and N'×384. N and N' should be close but they are not necessarily equal to each other.

Labeling of samples were formulated as the same sequential structure, in which human annotations of peak start/end will have values of 1 on corresponding tasks. Further label smoothing was applied to increase stability and robustness: sample points close to the human annotated label/ground $$\tilde{y} = \exp\left(-\frac{d_{RT}^2}{\sigma_{RT}} - \frac{d_{ABD}^2}{\sigma_{ABD}}\right)$$

truth start/end annotations will also have positive label values, calculated as:

$d_{RT}$ and $d_{ABD}$ are differences in retention time (RT) and differences in abundance (ABD) and $\sigma_{RT}$ and $\sigma_{ABD}$ are hyperparameters controlling the respective decay rates during training. The purpose of smoothing is to allow model adaptivity to noisy labels and/or account for human labeling/annotations that do not specify a single point. A neighborhood of points near the label however can represent reasonable points indicating transition from noise to signal as well.

5.4 Training Settings

Referring again to FIGS. 5A and 5B (MODEL A) and FIGS. 6A and 6B (MODEL B), MODEL A and MODEL B were implemented in Pytorch.

MODEL A contained two bi-LSTM layers with 128 features for hidden state, and LSTM outputs are then applied to a multi-head attention layer with 8 heads and 32 features in each head. Outputs from heads are concatenated and go through a fully-connected hidden layer with 32 units, then map to 2 tasks each with two classes through an affine layer. Softmax is applied to each task and each point in the sequence for generating probabilities of peak start/end. The model is trained by cross entropy loss between smoothed labels and the softmax predictions on the train subset containing 86311 samples for 20 epochs, with batch size of 8 and learning rate of 0.001. Early stopping is applied based on validation set performances.

MODEL B contained two sets of sequential network structure identical to the above, except for the fully connected layer, used to encode sample and reference respectively. Weights are not shared between the two structures. A sample-reference attention layer is applied on the sample encodings (as queries), reference encodings (as keys) and reference labels (as values), the output of which will be of the same length as sample encodings and 2 on the task dimension. This is directly used as model predictions for peak start/end probabilities. Another loss term is calculated as KL divergence between the sample-reference attention map and a standard mapping which connects points with same retention time in sample and reference (similar to an identity matrix). The model is trained by the cross entropy loss plus an extra divergence term on the same training set under same settings.

Additional Definitions

As used herein a "processor" should be taken to include one or a plurality of processors used to perform a task, such as executing SAS program code, processing data for a GUI, or reading or writing from memory and includes a general purpose computer.

As used herein a "user" should be taken to include an actual person using an application locally, or accessing the application remotely using a web browser using a computer located remotely.

As used herein, a "computer" should be taken to include computers that have a hard disk drive for reading from and writing to a hard disk, a magnetic disk drive for reading from or writing to a removable magnetic disk, and an optical disk drive for reading from or writing to a removable optical disk such as a CD ROM, DVD, or other optical media. The hard disk drive, magnetic disk drive, and optical disk drive are connected to the system bus by a hard disk drive interface, a magnetic disk drive interface, and an optical drive interface, respectively. The drives and their associated computer-readable media provide nonvolatile (non-transitory) storage of computer readable instructions, data structures, programs, and other data for the computer system.

As used herein, a "database" should be taken to include a centralized or distributed database and includes a SQL database.

As used herein, the term "data" should be taken to include any information contained in machine readable memory of a file system or used in a database or other structured data, or unstructured data representation in transitory or non-transitory memory.

As herein used, an "input device" should be taken to include a keyboard, mouse, pointer, touch pad, voice recognizer or other forms of input devices connected to a computer (with or without a display) for making modifications to, exploring, accessing, or generating electronic content that may be stored in memory.

As herein used, "display" is an LCD/LED type display or other types of display devices connected to the computer and capable of rendering and receiving input using a GUI or displaying other information generated by an application running on the computer executing machine executable code.

As used herein, "module" or "component" should be taken to include a software or source code file, or set of machine-executable instructions contained, or not contained in a source code file and existing on a non-transitory or transitory memory medium. A module may exist as a stand-alone program or represent a program called by another program. A "component" is a portion of a "module" in the sense that the module calls a component to perform a task or task(s) portion of the module.

A "data repository" or "repository" as used and construed can include a database, data store, data warehouse, data lake or a combination of these things.

As used herein "memory" should be taken to include a machine-readable medium, either transient computer-readable storage medium or non-transient computer-readable storage medium. In various embodiments, the volatile (transient) portion of memory may be implemented using any suitable memory technology, such as static random access memory (SRAM), synchronous dynamic RAM or any other type of memory. While the examples of memory as shown and described may refer to a single machine-readable medium, memory should be taken to include a single medium or multiple media (e.g., a centralized or distributed database, and/or associated caches and servers, and or a variety of storage media, such as the processor registers, memories, and the storage device) that store one or more sets of machine-executable code or data. The term "machine-readable medium" shall also be taken to include any medium that is capable of storing, encoding or carrying a set of instructions for execution by the machine and that cause the machine to perform any one or more of the methodologies of the present invention, or that is capable of storing, encoding or carrying data structures utilized by or associated with such a set of instructions. The term memory shall accordingly be taken to include tangible media, such as solid-state memories and optical and magnetic media.

As used herein "module" should be taken to include a unit of distinct functionality that can provide information to, and receive information from, other modules. Accordingly, described modules may be regarded as being communicatively coupled. Modules may also initiate communication with input or output devices, and can operate on a resource (e.g., a collection of information, such as a database). Modules may include hardware circuitry, optical components, single or multi-processor circuits, memory circuits, software program modules and objects, firmware, and combinations thereof, as appropriate for particular implementations of various embodiments. The term "module" can include an identifiable portion of code, data, or a computational object to achieve a particular function, operation, processing, or procedure.

In some examples, set forth herein is a method for diagnosing a disease comprising
quantifying mass spectrometry transitions, wherein the transitions are m/z intensity value peaks characteristic of glycopeptides or peptides comprising an amino acid sequence, and analyzing the quantification using a model to determine a probability that the sample is or isn't within a disease classification based on the quantification. In some of these examples, the transitions, glycopeptides, peptides, amino acid sequences, or any combination thereof may be those set forth in International PCT Patent Application No. PCT/US2020/0162861, filed Jan. 31, 2020.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in claims should not be construed to limit the invention to the specific embodiments disclosed in the specification.

What is claimed is:

1. A method of training a model to identify mass spectrometry peaks comprising:
   using a plurality of labeled sequential data, each of the plurality of labeled sequential data comprising a peak start and a peak stop label representing retention time values characteristic of glycopeptides or peptides, or fragments thereof; and
   training at least one machine learning model using the labeled sequential data, wherein the trained machine learning model is adapted for identifying mass spectrometry peak start and peak stop points indicating the presence of one or more glycopeptides or peptides, or a fragment thereof, present in a biologic sample.

2. The method of claim 1, further comprising quantifying the presence of the one or more glycopeptides or peptides by integration over time between the mass spectrometry peak start and peak stop points from the biologic sample.

3. The method of claim 1, wherein the machine learning model is a recurrent neural network model.

4. The method of claim 3, wherein the recurrent neural network model is a bi-directional LSTM recurrent neural network model with attention layer.

5. A method comprising computing an abundance for a glycopeptide or peptide using a machine learning model trained by the process of claim 1.

6. A system comprising
a data repository of labeled sequential data;
one or more processors coupled to the data repository;
machine executable code, residing in non-transitory memory accessible to the one or more processors, that when executed by the one or more processors performs the method of claim 1.

7. The method of claim 1, wherein the machine learning model is a sequential model, MODEL A, or a reference-based model, MODEL B.

8. The method of claim 1, wherein mass spectrometry peak start and peak stop points are identified.

9. The method of claim 1, wherein the mass spectrometry peak start and peak stop points are from tandem chromatography-mass spectrometry data.

10. A method of identifying mass spectrometry peaks comprising:
    providing at least one trained neural network model that produces an output as a function of input parameters, wherein values for the input parameters comprise a sequence of retention time values for a glycopeptide or peptide having a mass-to-charge ratio m/z; and
    providing as values for the input parameters mass spectrometry (MS) data comprising mass-to-charge ratios m/z over the sequence of retention time values from a mass spectrometry of a biologic sample;
    wherein the output comprises a location for one or more peak start and peak stop retention time values indicating the presence of one or more analytes, or a fragment thereof, in the biologic sample.

11. A system, comprising
a data repository of mass spectrometry (MS) data;
one or more processors coupled to the data repository;
machine executable code, residing in non-transitory memory accessible to the one or more processors, that when executed by the one or more processors performs the method of claim 10.

12. The method of claim 10, wherein peak start and peak stop retention time values of the mass spectrometry peaks are identified.

13. The method of claim 10, further comprising quantifying the presence of one or more glycopeptides or peptides by summing or integration over retention time values between the identified peak start and peak stop retention time values from the biologic sample.

14. The method of claim 13, wherein the quantifying step comprises applying a weighted smoothing function over the identified peak start and peak stop retention time values.

15. The method of claim 10, wherein a confidence score is calculated for the identified peak start and peak stop retention time values, wherein if the value of the confidence score is below a threshold value, the identified peak start and peak stop retention time values are excluded from analysis.

16. The method of claim 15, wherein the identified peak start and peak stop retention time values that are excluded from analysis are targeted for reevaluation by a human.

17. The method of claim 10, wherein the mass spectrometry (MS) data is tandem chromatography-mass spectrometry data.

18. The method of claim 10, wherein the trained neural network model is a sequential model, MODEL A, or a reference-based model, MODEL B.

19. A method, comprising
computing a distribution of probabilities over a sequence of points representing mass spectrometry (MS) data for a given mass-to-charge ratio m/z and retention time period, the probabilities representing a likely peak start or peak stop retention time; and
computing a statistic for the abundance using the distribution of probabilities, wherein the statistic is indicative of the presence of a biologic sample in the mass spectrometry (MS) data.

20. The method of claim 19, wherein the statistic is a mean abundance computed as a weighted sum of integrals using all possible pairs of start and end points for evaluating the integral.

21. The method of claim 19, wherein the mass spectrometry (MS) data is tandem chromatography-mass spectrometry data.

\* \* \* \* \*